(12) United States Patent
Takeuchi

(10) Patent No.: US 7,366,343 B2
(45) Date of Patent: Apr. 29, 2008

(54) PATTERN INSPECTION METHOD AND APPARATUS

(75) Inventor: Naoya Takeuchi, Hachioji (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 779 days.

(21) Appl. No.: 10/781,101

(22) Filed: Feb. 17, 2004

(65) Prior Publication Data

US 2004/0179727 A1 Sep. 16, 2004

(30) Foreign Application Priority Data

Mar. 10, 2003 (JP) ............................. 2003-063934

(51) Int. Cl.
*G06K 9/00* (2006.01)

(52) U.S. Cl. .................. 382/145; 348/87; 356/237.2; 382/144; 382/218; 716/19

(58) Field of Classification Search ................ 382/145, 382/147, 149, 151, 144, 218; 348/87; 356/237.2; 716/19
See application file for complete search history.

(56) References Cited

U.S. PATENT DOCUMENTS

| | | | |
|---|---|---|---|
| 5,173,719 A | 12/1992 | Taniguchi et al. | |
| 5,600,734 A * | 2/1997 | Okubo et al. ............... | 382/147 |
| 6,169,282 B1* | 1/2001 | Maeda et al. ............... | 250/310 |
| 7,031,511 B2* | 4/2006 | Asai ........................... | 382/149 |
| 7,032,208 B2* | 4/2006 | Yamashita .................. | 716/19 |
| 7,113,629 B2* | 9/2006 | Onishi ........................ | 382/149 |
| 2002/0181760 A1* | 12/2002 | Asai ........................... | 382/149 |
| 2003/0197857 A1* | 10/2003 | Yamashita ............... | 356/237.2 |
| 2004/0179727 A1* | 9/2004 | Takeuchi .................... | 382/145 |
| 2005/0082476 A1* | 4/2005 | Hiroi et al. ................. | 250/310 |
| 2005/0094862 A1* | 5/2005 | Shimura ..................... | 382/141 |
| 2005/0147287 A1* | 7/2005 | Sakai et al. ................ | 382/141 |
| 2005/0172255 A1* | 8/2005 | Tsuchiya et al. .............. | 716/19 |
| 2005/0233601 A1* | 10/2005 | Tsuchiya et al. ............ | 438/800 |
| 2006/0002604 A1* | 1/2006 | Sakai et al. ................ | 382/141 |
| 2006/0147104 A1* | 7/2006 | Horie et al. ................ | 382/144 |

FOREIGN PATENT DOCUMENTS

| | | |
|---|---|---|
| JP | 2001-35893 | 2/2001 |
| JP | 3187827 | 7/2001 |

OTHER PUBLICATIONS

Patent Abstracts of Japan, Publication No. 2001-035893, dated Feb. 9, 2001, in the name of Masanori Ito et al.

* cited by examiner

*Primary Examiner*—Gregory M Desire
(74) *Attorney, Agent, or Firm*—Christie, Parker & Hale, LLP

(57) ABSTRACT

A pattern inspection method and a pattern inspection apparatus, which has an improved precision in detecting and correcting the positional deviation of images for a die comparison, have been disclosed. The quantity of correction of positional deviation of the images for the die comparison is determined based on the positional information of the images at multiple separate places in a die (pattern). For example, the multiple separate places include the vicinities of both ends in the pattern arrangement to be scanned in the die, and the part where the inspection is not completed yet. When the positional information of the part where the inspection is not completed yet is used, the correction of the positional relation of the images to be compared and the comparison of the images are started immediately after the capture of the images of two patterns is completed.

9 Claims, 17 Drawing Sheets

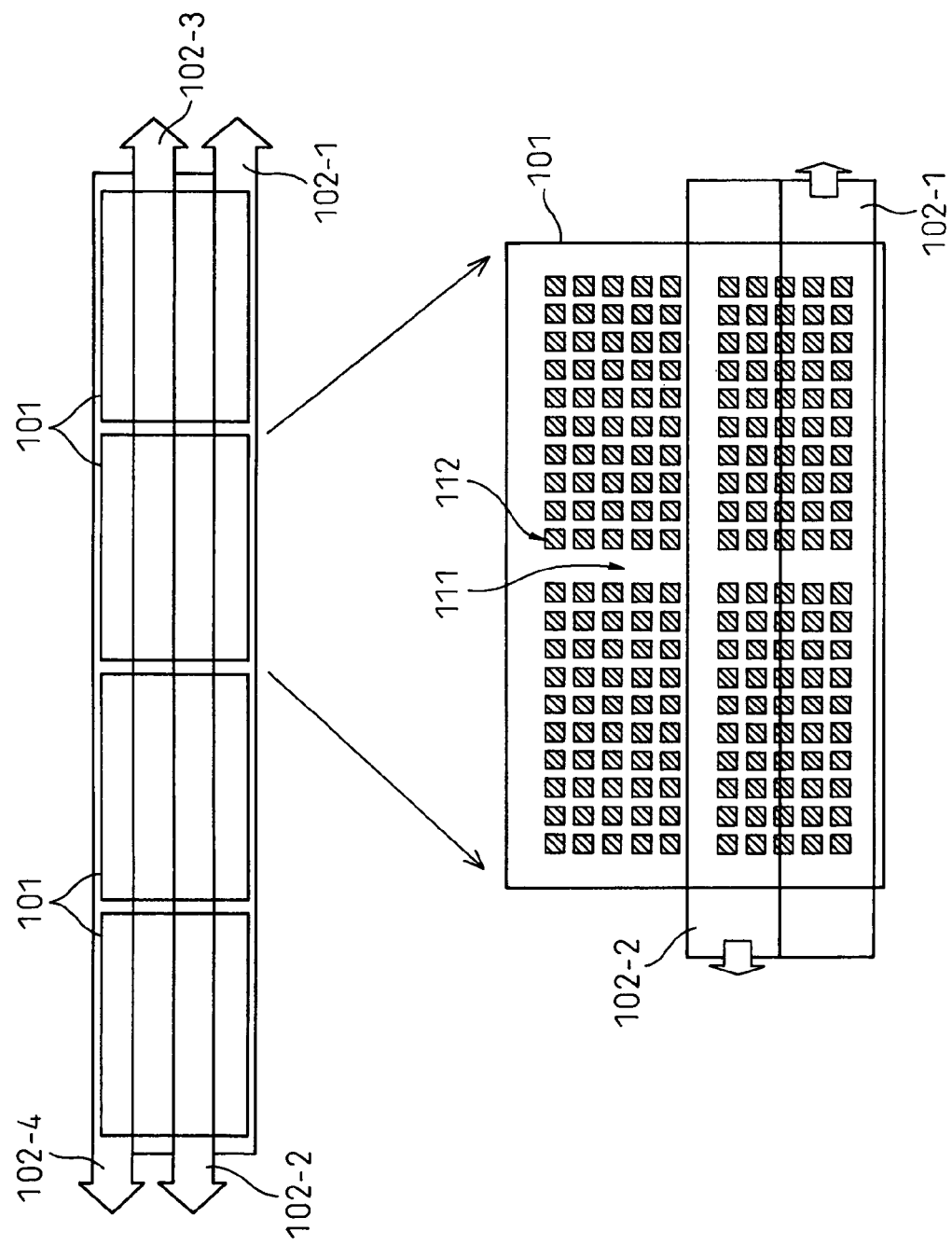

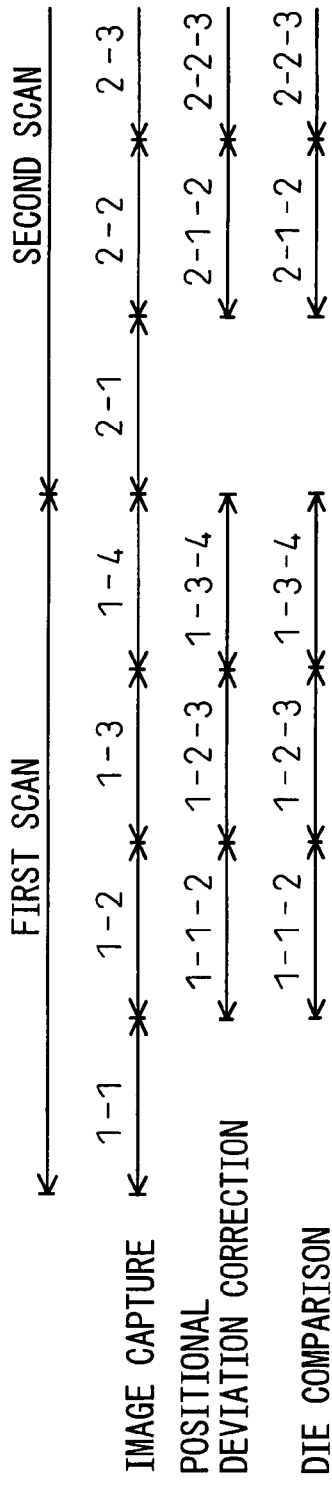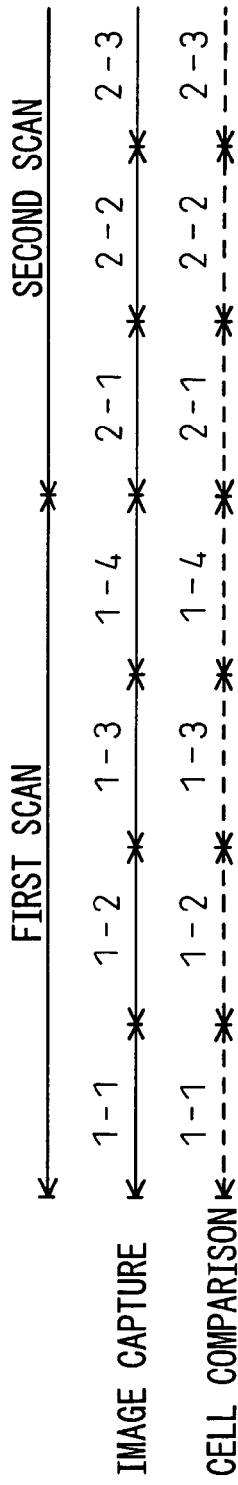

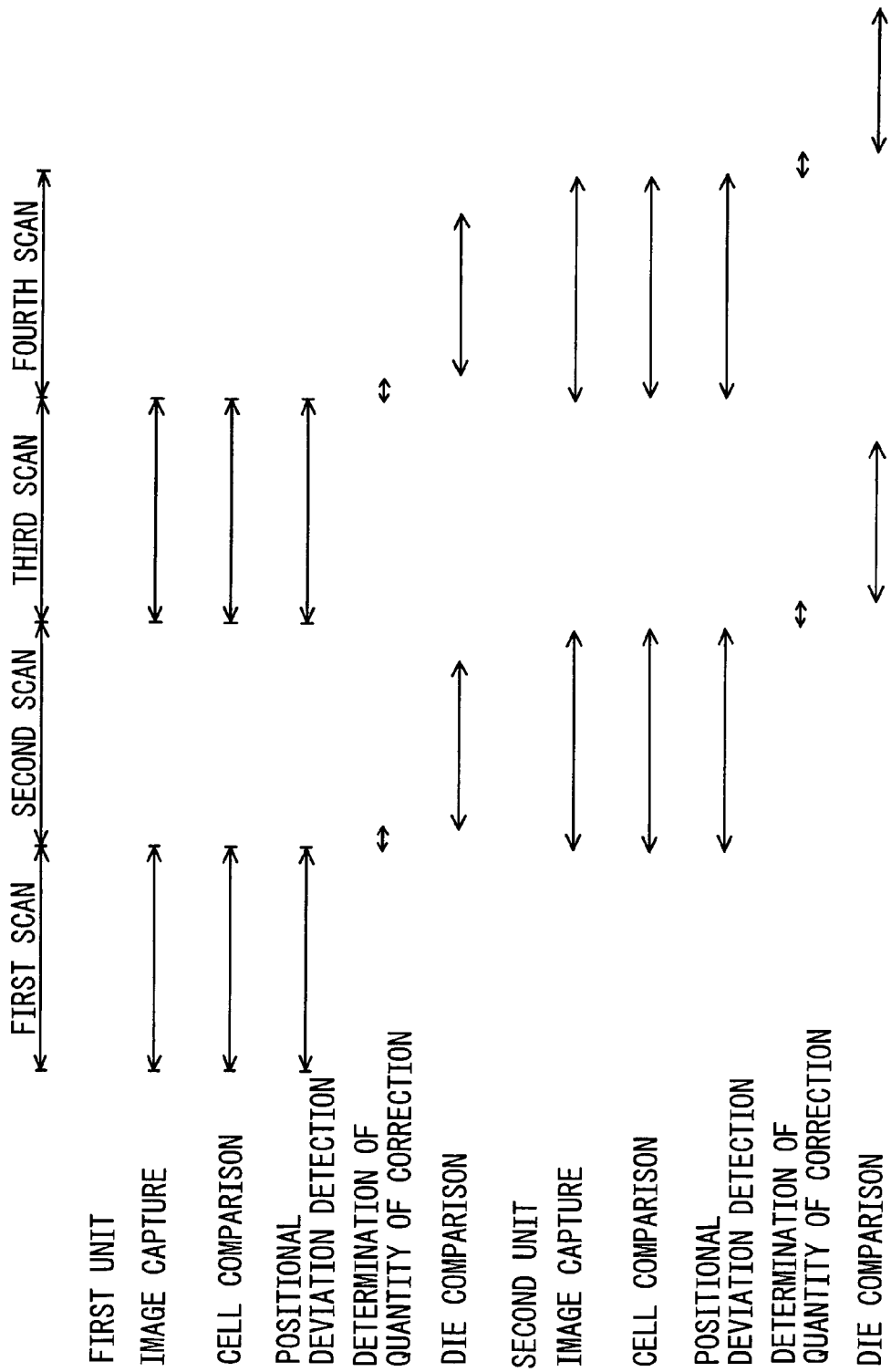

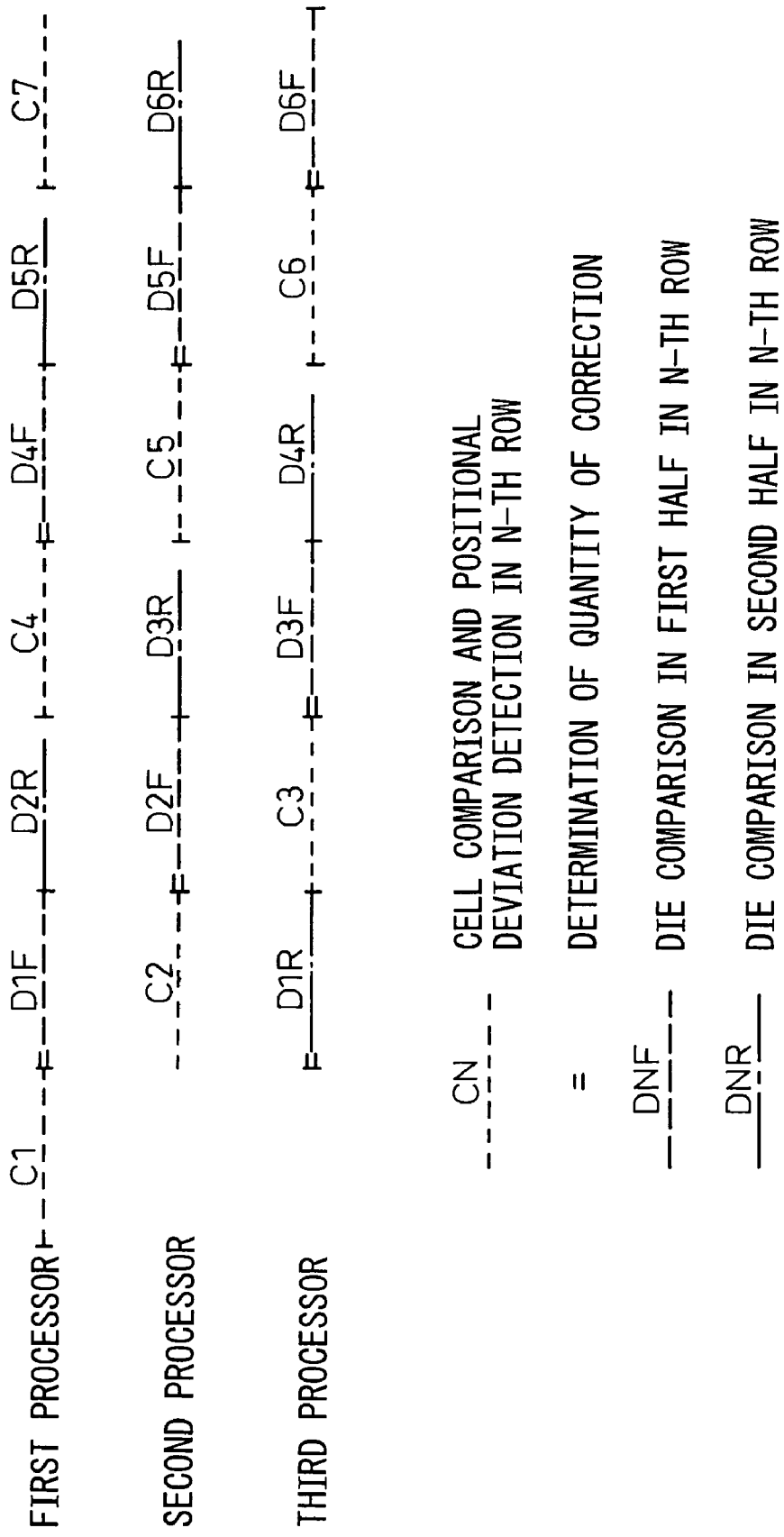

ent occurs, and then the comparison between the die 101-2 and a die 101-3 is made and the result is that a disagreement occurs at the same part, the part in the die 101-2 is judged to have a defect. Similarly, the comparison between the die 101-3 and a die 101-4 is made, and thus the comparison between neighboring dies is repeated sequentially.

PATTERN INSPECTION METHOD AND APPARATUS

CROSS-REFERENCE TO RELATED APPLICATION

This application claims priority of Japanese Patent Application Number 2003-063934, filed on Mar. 10, 2003.

BACKGROUND OF THE INVENTION

The present invention relates to a pattern inspection method and a pattern inspection apparatus. More particularly, the present invention relates to a pattern inspection method and a pattern inspection apparatus for obtaining multiple pattern images by scanning an object to be inspected on which multiple patterns which should be essentially the same are arranged regularly, such as a semiconductor wafer on which semiconductor chips (dies) are formed, and for making a comparison between neighboring patterns.

On a semiconductor wafer, a plurality of identical chips (dies) are formed in a regular arrangement. In the manufacturing process of a semiconductor device, whether a defect occurs in the formed die is inspected during the process or at the end of the process, and information about occurrence of a defect is immediately fed back to the manufacturing process in order to improve the yield. For this purpose, an inspection of the occurrence of a defect in a pattern is generally carried out by capturing the optical pattern of a die. In order to obtain an image with high resolution, the image of a semiconductor wafer is projected onto a one-dimensional image sensor and the image of the semiconductor wafer is formed by relatively moving the semiconductor wafer and the one-dimensional image sensor for scanning. FIG. 1 is a diagram showing an example of a scanning path for capturing the image of a semiconductor wafer 100 on which a plurality of dies 101 are formed in a regular arrangement. As shown in FIG. 1, on the semiconductor wafer 100, a plurality of the semiconductor chips (dies) 101 are formed in a regular arrangement and scanning is carried out along a scanning path 102 for capturing the image of the entire surface of the semiconductor wafer 100. According to this scanning path, after the lower portion of a die in a row is scanned to the right one after another, the upper portion of the die in the same row is scanned to the left, but a modification such as one in which after the lower portion of a die in a row is scanned to the right one after another, the lower portion of a die in the next row is scanned to the left.

FIG. 2 is a diagram for explaining in detail how scanning is carried out. In this example, the image of the die 101 in a row is captured in four scans 102-1 to 102-4. For example, in the case of a memory, each die 101 has a peripheral circuit part 111 and a cell part 112, as shown schematically. The peripheral circuit part 111 has a random (non-repeating) pattern, but the same cell pattern is repeated at a predetermined pitch at the cell part 112.

Inspection methods for detecting a pattern defect include a method in which a captured pattern of each die is compared with a reference pattern, but a general method currently employed is such one in which the corresponding patterns of neighboring dies are compared and when the two patterns coincide with each other, the pattern is judged to have no defect and when not, it is judged that one die has a defect. As described above, two patterns to be compared with each other should be essentially the same and it is rare for a defect to occur, therefore, such an inspection method is possible.

FIG. 3A to FIG. 3C are diagrams for explaining the defect inspection method when the same pattern is arranged regularly, as described above. The comparison between the patterns of two dies, which is made once, is called a single detection. The single detection cannot judge as to which die is defective when the patterns do not coincide with each other. Therefore, the comparison is made twice as shown in FIG. 3A, that is, the comparison between a die and one of neighboring dies is made and then the comparison between the die and the other neighboring die is made. This is called the double detection. When a die is judged to disagree with its neighboring dies on both sides by double detection, the die is judged to have a defect. For example, when the comparison between a die 101-1 and a die 101-2 is made and the result is that the difference in two pieces of image data of a certain part exceeds a threshold value and a disagreement occurs, and then the comparison between the die 101-2 and a die 101-3 is made and the result is that a disagreement occurs at the same part, the part in the die 101-2 is judged to have a defect. Similarly, the comparison between the die 101-3 and a die 101-4 is made, and thus the comparison between neighboring dies is repeated sequentially.

As shown in FIG. 2, the peripheral circuit part 111 has a random pattern, but the cell part 112 has the same cell pattern repeated at a predetermined pitch. Therefore, the peripheral circuit part 111 is inspected by making the die comparison, which is made between neighboring dies as described above, but the cell part 112 is inspected by making the double detection, in which an image is split at the repetitive period P of the cell pattern and a comparison is made sequentially between neighboring cell patterns. This is called cell comparison. FIG. 3B is a diagram for explaining cell comparison in which the cell pattern is repeated at a pitch of P and the comparison between neighboring cell pattern is sequentially made in such a way that the comparison between a cell pattern 121-1 and a cell pattern 121-2 is made, then the comparison between the cell pattern 121-2 and a cell pattern 121-3 is made, and so on. The cell comparison has the advantage of being unlikely to receive the influence of noise caused by the variations in colors of a wafer and the positional deviations of images because patterns are compared, the distance between which is relatively shorter than that in the case of the die comparison, therefore, it is possible for the cell comparison to have a high detection sensitivity. Because of this, it is desirable to make an inspection of the cell part at which the cell pattern is repeated by the cell comparison and make an inspection of the rest of the part, that is, the peripheral circuit part by the die comparison.

When patterns are compared, it is required that the positions to be compared coincide with each other. The cell comparison is made within the pattern of a die and the cell patterns to be compared are near to each other, therefore, it is possible to easily make the positions of two cell patterns coincide with each other if the repetitive pitch of the cell pattern is known. To be specific, images a pitch of P apart from each other are compared successively in the cell part.

In contrast to this, in the die comparison, a comparison is made between dies. As patterns of each die are exposed by a stepper or the like, the precision in the arrangement depends on the precision in movement of a moving mechanism in a stepper or the like and the distortion of a wafer caused during processing, and an error to a certain extent is inevitable. Therefore, the die comparison is made after the positional deviation is detected and corrected so that the patterns to be compared are made to coincide with each other.

FIG. 3C is a diagram for explaining the conventional positional deviation detecting and correcting process. When the die comparison is made, the image area defined by the width of the scan and a predetermined length in the scanning direction is called the frame, and it is general to make a comparison for each frame. In FIG. 3C, reference numbers 1-F1 and 1-F2 denote the frame of the first die and 2-F1 and 2-F2 denote the corresponding frame of the second die. The die comparison is made on a frame basis and the positional deviation detecting and correcting process is also carried out on a frame basis. To be specific, one of the patterns is moved so that the difference between the two patterns at a certain part in a frame is minimized, and in this case the positional deviation corresponds to the quantity of movement, and the comparison is made with the image moved by the quantity of movement. Either way, conventionally, the positional deviation detecting and correcting process was be carried out on the part to be compared immediately before the comparison.

FIG. 4 is a diagram showing the internal configuration for making the die comparison inspection in a conventional pattern inspection apparatus (inspection machine) of a semiconductor wafer. As will be described later, such a configuration is generally realized as an image processing unit by the use of a computer. The configuration and the operation required for making the die comparison inspection are briefly explained below.

An object to be inspected (wafer) 13 is retained by a chuck 12 capable of moving (in the X and Y directions) and adjusting rotation angles (θ) by means of an XYθ stage 11. Light from a lamp 17 is guided to the wafer 13 to be irradiated wherewith via a beam splitter 16, a tube lens 15 and an optical microscope 14, and the reflected image is projected onto a TDI camera 18 via the optical microscope 14, the tube lens 15, and the beam splitter 16. The TDI camera is used in order to increase the scan speed by improving brightness, but a normal one-dimensional CCD camera may be used instead. In the image capturing section configured as above, the wafer 13 is moved at a constant speed in the scanning direction by means of the XYθstage 11, and an image signal is generated from the TDI camera 18 in a cycle in accordance with the moving speed. The generated image signal is converted into multi-value image data in an A/D converter 19.

The image data is sent to an image delaying memory 21 for temporarily storing image data equivalent to a die, a difference detecting section 23 for calculating the difference in image data between two neighboring dies and an automatic picture alignment section (AP processing section) 22 for correcting the positions of the two pieces of image data from an image capturing section 20.

The image delaying memory 21 temporarily stores image data equivalent to a die and outputs the image data, which the AP processing section 22 stores in synchronization with the capture of the image data of the next die, after delaying by an amount equivalent to a die. The AP processing section 22 detects the positional deviation in the images of the same part (the same frame) of the image data of the die (second die) sent from the image capturing section 20 and the image data of the die (first die) preceding by one sent from the image delaying memory 21, that is, two neighboring dies, on a frame basis.

The difference detecting section 23 carries out the positional alignment of the image data of the first die and the second die based on the positional deviation information obtained by the AP processing section 22, compares the gray levels between corresponding pixels, and generates a gray level difference image.

A defect judging section 24 judges a pixel to be a defect candidate which has a gray level difference exceeding a predetermined threshold in the gray level difference image generated by the difference detecting section 23. At this time, it is not possible to specify the die on which the defect candidate exists between the first die and the second die because of the single detection, therefore, a single defect candidate image, which shows the position of the pixel judged to be a defect candidate by two values, is temporarily stored internally and when the image capture of the third die is started after a certain period of time delay, the similar comparison as described above is repeated between the second die and the third die to obtain the similar two-valued single defect candidate image, which is then compared with the stored single defect candidate image between the first die and the second die (double detection). If there exists a defect candidate within a certain allowable distance, the part corresponding to the pixel is stored in a defect candidate storage section 25 as a defect which exists in the second die.

The pattern inspection apparatus shown in FIG. 4 can be realized by the use of an operation circuit, but generally it is realized as an operation processing unit (computer) controlled by software by the use of a processor and memory. FIG. 5 is a diagram showing the hardware configuration of an operation processing unit. As shown schematically, an operation processing unit 30 includes the image capturing section 20, a memory 31 and a processor 34. The memory 31 includes an image memory 32 for storing image data and a defect information memory 33 for storing defect information, and further includes a working memory or the like for the processor 34 to carry out operation work. It is necessary for the image memory 32 to have a capacity for storing image data equivalent to at least one die and, actually, a memory capacity for several frames is required additionally. The processor reads image data from the image capturing section 20 and the corresponding image data of the die preceding by one in the image memory 32 on a frame basis, and carries out positional alignment and differential operation, and makes a judgment of the difference with respect to the threshold. The image data from the image capturing section 20 is overwritten to the image memory 32 one after another.

The configuration for making the cell comparison is almost the same as that for making the die comparison shown in FIG. 4, except in that the image delaying memory has a small capacity because the memory is required to store only one cell pattern and that the AP processing section 22 is not necessary because positional alignment adjustment is not carried out. When a die comparison section and a cell comparison section are realized by the use of the configuration shown in FIG. 5, the memory can be shared.

FIG. 6A is a time chart of a conventional example, showing the relationship of the process of each part when the die comparison is made by using the pattern inspection apparatus shown in FIG. 4. As shown schematically, this is an example where one scan covers four dies. In this example, the double detection is carried out only for the second and third dies during one scan, therefore, a defect can be detected from the second and third dies but not from the first and fourth dies. Various methods for carrying out the double detection for dies on both ends during a scan have been proposed and an example is a method in which the dies on both ends are compared with dies apart by two dies, respectively, or another example is a method in which the dies on both ends are compared with each other. When the same portion of the dies in the next row are scanned in the reverse direction in the next scan, a method is possible in which the dies on both ends are compared with those on both ends of the second row, but in this case, it is required that the stored image data can be read in the reverse direction.

As shown in FIG. 6A, the image capture is carried out successively from the die at one end to the die at the other contained in the same row during one scan. The positional deviation detection and correction and the die comparison are started after a delay equivalent to one die from the image capture and completed after a delay after the image capture of the last die at the end is completed. In other words, when the image capture of the first die is completed and the image capture of the second die is started, the positional deviation detection and correction and the die comparison are started. When the cell comparison is made separately, the die comparison is not required to be made for the cell part, therefore, when the operation speed of the processor is sufficiently high, there may be cases where the process is suspended while image data of the cell part is captured during the die comparison.

FIG. 6B is a time chart in a conventional example, showing the relationship of the process of each part when the cell comparison is made. The cell comparison is started after a delay equivalent to one cell pattern during image capturing of each die and completed after a delay after the image capture of the last cell pattern at the end is completed. Therefore, the cell comparison is completed when the image capture is completed in each die.

Conventionally, when the die comparison inspection and the cell comparison inspection are made for a wafer, the die comparison inspection is made first by scanning the entire surface of the wafer, then the cell comparison inspection is made by scanning the entire surface of the wafer because it is difficult to simultaneously make the die comparison and the cell comparison because of the lack of operation ability. Therefore, there is a problem that two scans of the entire surface of the wafer are required and the inspection time is lengthened.

Japanese Patent No. 3187827 has disclosed a pattern inspection method and a pattern inspection apparatus, which have a die comparison circuit and a cell comparison circuit, classifies an image into a part for the die comparison and a part for the cell comparison, and compares and inspects each part respectively using the corresponding circuit. FIG. 7 is a time chart of the process of the method and apparatus disclosed in Japanese Patent No. 3187827. As shown schematically, the cell comparison is made while capturing the image of each die, and the positional deviation correction and the die comparison are started after a delay equivalent to a die, and completed after the image capture of the last die at the end of the row is completed and a certain period of time elapses. When a pattern inspection apparatus, which makes the die comparison inspection and the cell comparison inspection at the same time during one scan, is made up of the processor and memory with sufficient processing ability as shown in FIG. 5, the time chart of each process is the same as that shown in FIG. 7.

As explained by referring to FIG. 3C, the positional deviation detection and correction of two images, for which the die comparison is made, are carried out on a frame basis. The width of the frame in the scanning direction corresponds to hundreds of pixels, which is as small as several thousandths of the width of a die. This is applicable to the technique disclosed in Japanese Patent No. 3187827. As the die comparison is made on a frame basis and two images to be compared are required to coincide with each other within the frame, the positional deviation detection and correction described above is basically sufficient.

However, there arises a problem that an image of a die has various factors which vary the image of each die, such as variations in color, and the detection of positional deviation is difficult to make when the number of patterns is small and, in an extreme case, the detection of positional deviation is made even for a part where a defect exists and the correction based on the detected result is made, therefore, the positional deviation detection and correction cannot be carried out precisely. Conventionally, the present die and the immediately preceding die are overlapped and coincidence is examined, but when a sufficient incidence cannot be obtained, the data of positional deviation of the preceding frame is, for example, used for correction. However, the preceding frame is very close and thought to have similar variations in color, therefore, the positional deviation detection and correction cannot be carried sufficiently precisely. If the correction of positional deviation is insufficient, the difference between two images becomes large even for parts with no defect, and, conversely, the difference becomes small where a defect exists and, therefore, the precision of detecting defects is degraded. As described above, the precision of the detection and correction of positional deviation are essential for the die comparison.

SUMMARY OF THE INVENTION

The first object of the present invention is to realize a pattern inspection method and a pattern inspection apparatus having the improved precision in the detection and correction of positional deviation in images for which the die comparison is made. The second object is to realize a pattern inspection method and a pattern inspection apparatus capable of effectively making both the die comparison and the cell comparison with the improved precision in the detection and correction of positional deviation in images for which the die comparison is made.

In order to realize the above-mentioned objects, a pattern inspection method and a pattern inspection apparatus according to a first aspect of the present invention is characterized in that the quantity of positional deviation correction of images, for which the die comparison is made, is determined based on positional information of images at multiple separate places in a die (pattern). For example, the multiple separate places include those near both ends of the pattern arrangement to be scanned in the die, and those places not scanned yet are also included.

In other words, the pattern inspection method according to the first aspect of the present invention is characterized in that an object to be inspected, in which a plurality of identical patterns are arranged, is scanned for capturing images, positional information of the images of neighboring identical patterns is detected, the quantity of correction, by which the positional relation of the images of the neighboring identical patterns is corrected, is determined based on the detected positional information, and the positional relation is corrected based on the quantity of correction and at the same time the corrected images are compared, wherein the quantity of correction is determined based on positional information of images at multiple separate places in the pattern.

The pattern inspection apparatus according to the first aspect of the present invention is characterized by comprising an image capturing section for capturing the images by scanning an object to be inspected, in which a plurality of identical patterns are arranged, an image storage section for storing the captured imaged, a positional information detecting section for detecting positional information of the images of neighboring identical patterns, a correction quantity determining section for determining the quantity of correction of the positional relation of the images of the neighboring identical patterns based on the detected positional information, and a pattern comparison section for comparing the images whose positional relation is corrected based on the quantity of correction, wherein the correction quantity determining section determines the quantity of correction based on positional information of images at multiple separate places in the pattern.

Generally, each die is exposed by the use of a common mask, therefore, the two dies to be compared have an identical pattern and, when a positional deviation exists between the images of the two dies, it is thought that such a positional deviation exists at all of the identical parts in the die. Therefore, if the quantity of correction is determined based on positional information (information about positional deviation) of images at multiple places in a die (pattern) as in the first aspect of the present invention, a more precise positional deviation correction can be realized.

For example, if the positional deviation at one end of a die and that at the other are detected and the quantity of change is calculated, the positional deviation at a place between both ends or beyond the ends can be thought to change at the same rate of change, therefore, the positional deviation at every place can be calculated by the use of the interpolation method or the extrapolation method. Moreover, the calculation is made for two places apart from each other, the precision of calculation of the quantity of change is improved. For example, if there exists a positional deviation of five pixels across 100 frames, the deviation per frame is 0.05 pixels, and it is possible to correct a deviation using a value of 0.05 pixels, whereas it is difficult to detect such a deviation by detecting the positional deviation only between frames as is done conventionally.

When variations in color are great at a certain place, it is possible to precisely detect the positional deviation of the entire die even if the data of the place is not used for positional deviation detection.

Moreover, as the positional deviation can be thought to be the same for the entire die, if the positional deviation data at least at two places is obtained, the positional deviation for the entire die can be calculated, therefore, it is not necessary to detect positional deviation on a frame basis and the number of places for which positional deviation is detected can be considerably reduced compared to the conventional case, and the burden of operation can be reduced accordingly.

In the first aspect of the present invention, the comparison after the determination of the quantity of correction of positional deviation can be started after all the images of two dies (patterns) to be compared are captured, and it is necessary for the image of one of the dies to be delayed by an amount equivalent to two dies, and for the image of the other to be delayed by an amount equivalent to one die. Therefore, the correction of the positional relation of neighboring patterns and the comparison of images are started after the capture of the images of the two neighboring patterns is completed.

A pattern inspection method and a pattern inspection apparatus according to a second aspect of the present invention are characterized in that the quantity of positional deviation correction of images, for which the die comparison is made, is determined based on positional information of images of multiple separate dies in each row in the scanning direction in the die arrangement. For example, the multiple separate dies are those at both ends, which include portions in each row for which inspection is not completed yet.

In other words, the pattern inspection method according to the second aspect of the present invention is characterized in that an object to be inspected, in which a plurality of patterns are arranged, is scanned for capturing images, positional information of the images of patterns in each row is detected, the quantity of correction, by which the positional relation of the images of the neighboring patterns is corrected, is determined based on the detected positional information, and the images, whose positional relation is corrected based on the determined quantity of correction, are compared, wherein the quantity of correction is determined based on positional information of images of multiple separate patterns in each row in the scanning direction in the pattern arrangement.

The pattern inspection apparatus according to the second aspect of the present invention is characterized by comprising an image capturing section for capturing images by scanning an object to be inspected in which a plurality of patterns are arranged, an image storage section for storing captured images, a positional information detecting section for detecting positional information of the images of the patterns in each row, a correction quantity determining section for determining the quantity of correction of the image positions of neighboring patters based on the detected positional information, and a pattern comparison section for comparing the images whose positional relation is corrected based on the determined quantity of correction, wherein the correction quantity determining section determines the quantity of correction based on positional information of the images of the multiple separate patterns in each row in the scanning direction in the pattern arrangement.

Each die is exposed while a stepper or the like shifts the exposure position. The moving mechanism of an exposure apparatus, such as a stepper, is very precise and each die is formed into a regular arrangement on a wafer. The moving mechanism of a pattern inspection apparatus is also very precise and if the arrangement position of dies on the wafer is viewed in terms of the coordinates of the moving mechanism of a pattern inspection apparatus, it is possible to regard that the coordinates are transformed linearly. Therefore, if the quantity of correction is determined based on information of the relative positions (positional deviation information) of the images of multiple separate dies (patterns) in a row, as in the second aspect of the present invention, the positional deviation can be corrected more highly precisely.

For example, if the position of the die at one end and that of the die at the other in a row are detected and the quantity of change is calculated, the positional deviation of a die in the area between the dies and moreover, a die outside the area can be thought to change at the same rate of change, therefore, it is possible to calculate the positional deviation of any die by the use of the interpolation or extrapolation method. In addition, the two dies apart from each other are used for the calculation, the precision of the calculation of the quantity of change is improved.

In the second aspect of the present invention, the comparison after the determination of the quantity of positional deviation correction can be started after all of the images of the dies (patterns) in a row are captured, and it is necessary for the image of a die to be delayed by an amount equivalent to one row.

When the cell comparison is also made, the cell comparison is made in parallel to the capture of the images to be used in the subsequent comparison immediately after the capture of the images of neighboring cell patterns in each die (pattern).

A pattern inspection apparatus according to a third aspect of the present invention is an apparatus which carries out the pattern inspection method according to the second aspect and which is characterized by having two processing units, wherein the two processing units alternately carry out storing of images, the cell comparison and the positional deviation detection, and the correction of positional relation and the pattern comparison.

In other words, the pattern inspection apparatus according to the third aspect of the present invention is characterized by comprising an image capturing section for capturing images by scanning an object to be inspected on which a plurality of patterns having a cell pattern repeated at a prescribed pitch are arranged, and first and second processing units having the same configuration, wherein each processing unit has an image storage section for storing captured images, a positional information detecting section for detecting the positional information of pattern images in each row, a correction quantity determining section for determining the quantity of correction by which the positional relation of images of neighboring patterns is corrected based on the detected positional information, a pattern comparison section for comparing the images whose positional relation has been corrected based on the determined quantity of correction, and a cell comparison section for comparing the neighboring cell patterns in each pattern, wherein the first processing unit and the second processing unit alternately carry out storing of the images, the cell comparison and the positional deviation detection, and the determination of the quantity of correction and the pattern comparison.

The pattern inspection apparatus according to the third aspect of the present invention carries out the pattern inspection method according to the second aspect and at the same time has the processing units having the same configuration, therefore, the configuration is practically simple and can be realized at a low cost.

BRIEF DESCRIPTION OF THE DRAWINGS

The features and advantages of the invention will be more clearly understood from the following description taken in conjunction with accompanying drawings, in which:

FIG. 2. is a diagram showing in more detail how a die on a wafer is scanned;

FIG. 6A and FIG. 6B are time charts showing the action of each part during the die comparison inspection and the cell comparison inspection in the conventional pattern inspection apparatus;

FIG. 14 is a time chart showing the action of each part in the pattern inspection apparatus in the third embodiment;

FIG. 16 is a time chart showing the action of each part in the pattern inspection apparatus in the fourth embodiment.

DESCRIPTION OF THE PREFERRED EMBODIMENTS

Figure 1:
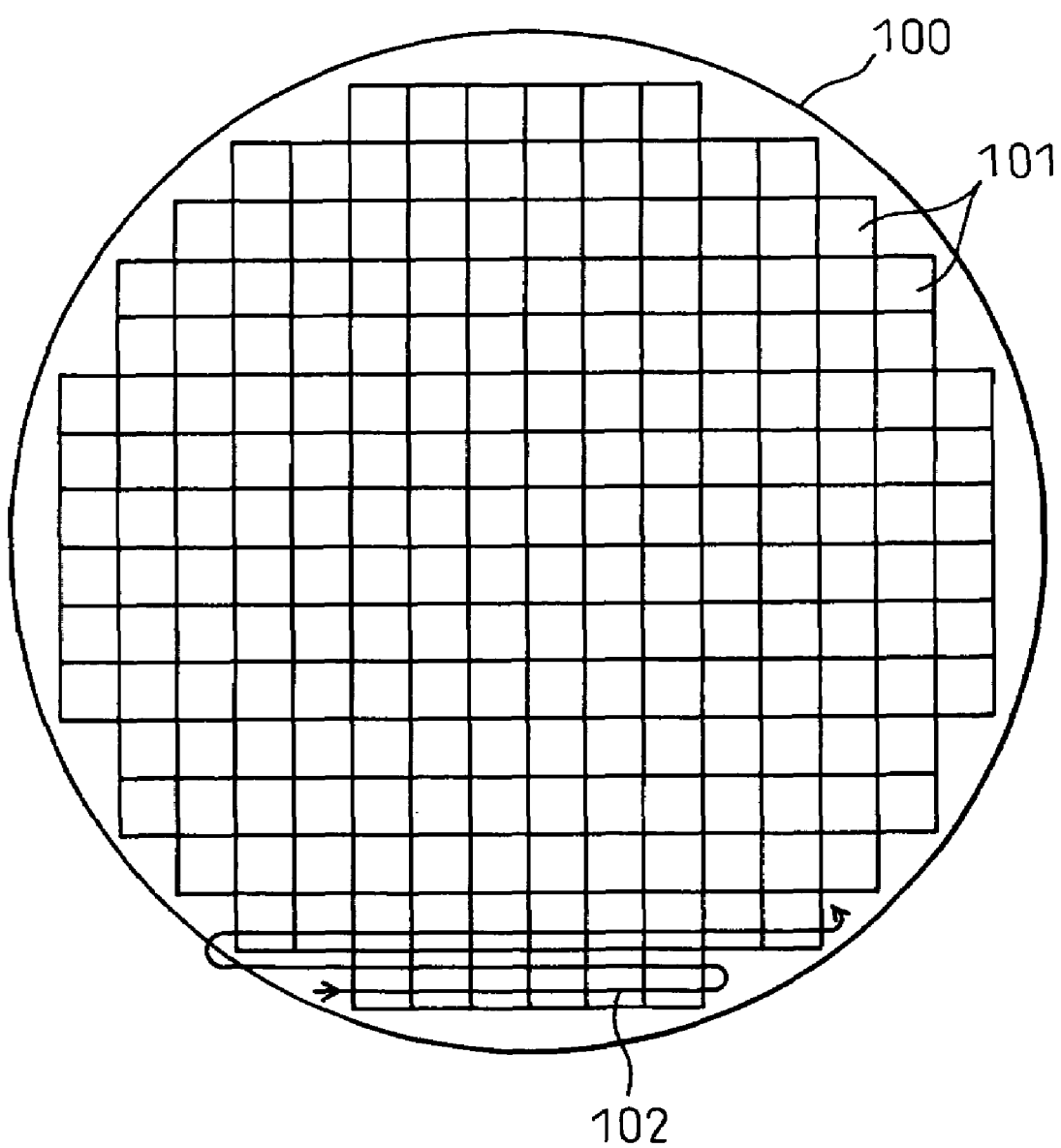
FIG. 1 is a diagram showing a scan path for capturing and inspecting patterns of a chip (die) on a semiconductor wafer.
Figure 3A:
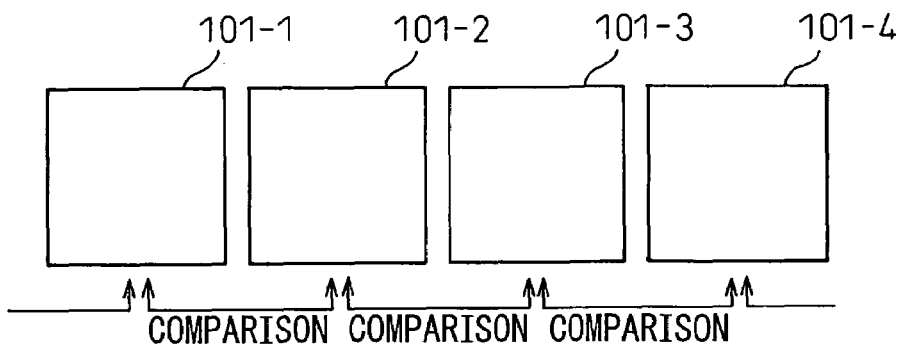
FIG. 3A to FIG. 3C are diagrams for explaining a die comparison, a cell comparison, and the positional deviation detection and correction for the die comparison in a conventional case.
Figure 3B:
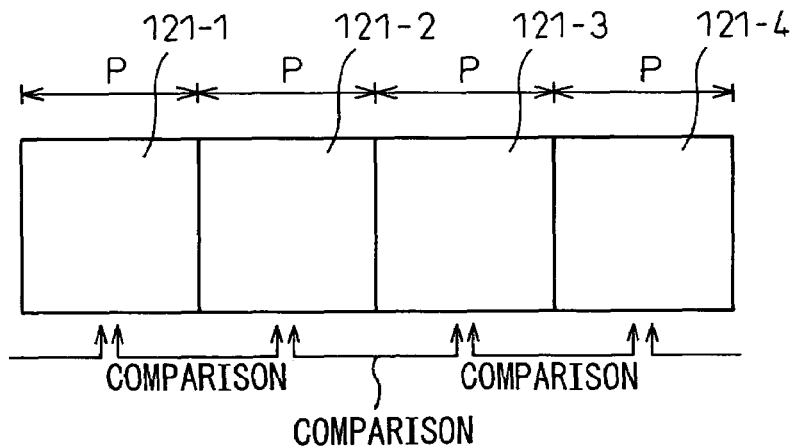
Figure 3C:
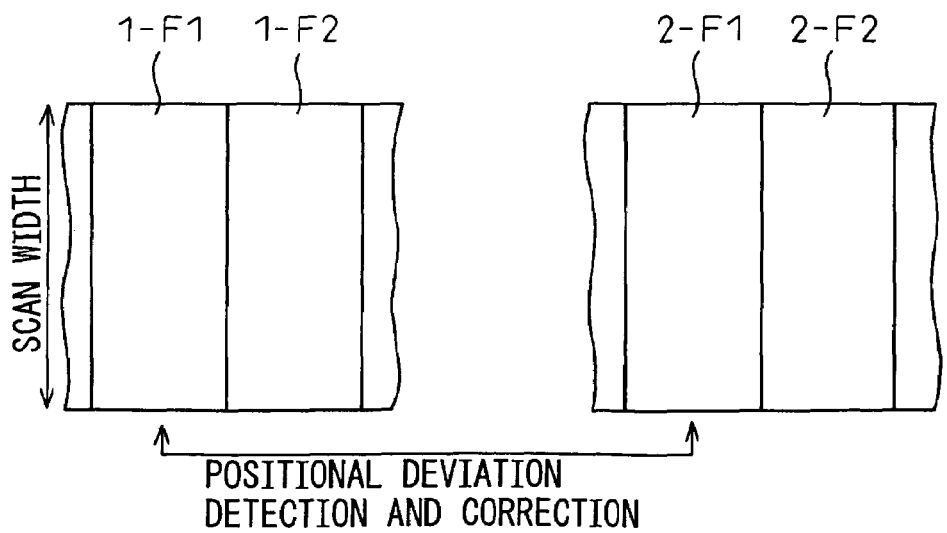
Figure 4:
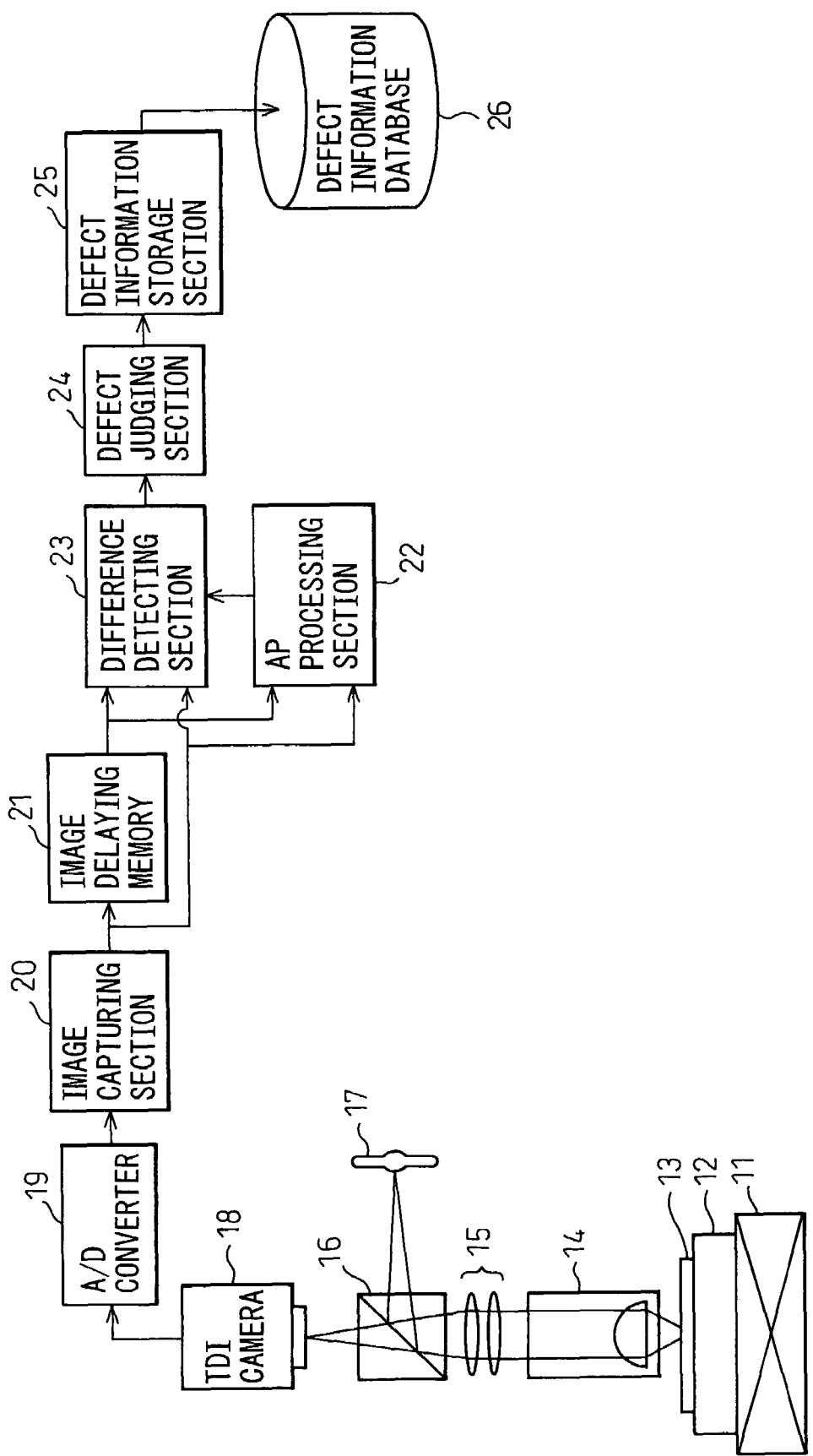
FIG. 4 is a diagram showing the configuration of a conventional pattern inspection apparatus.
Figure 8:
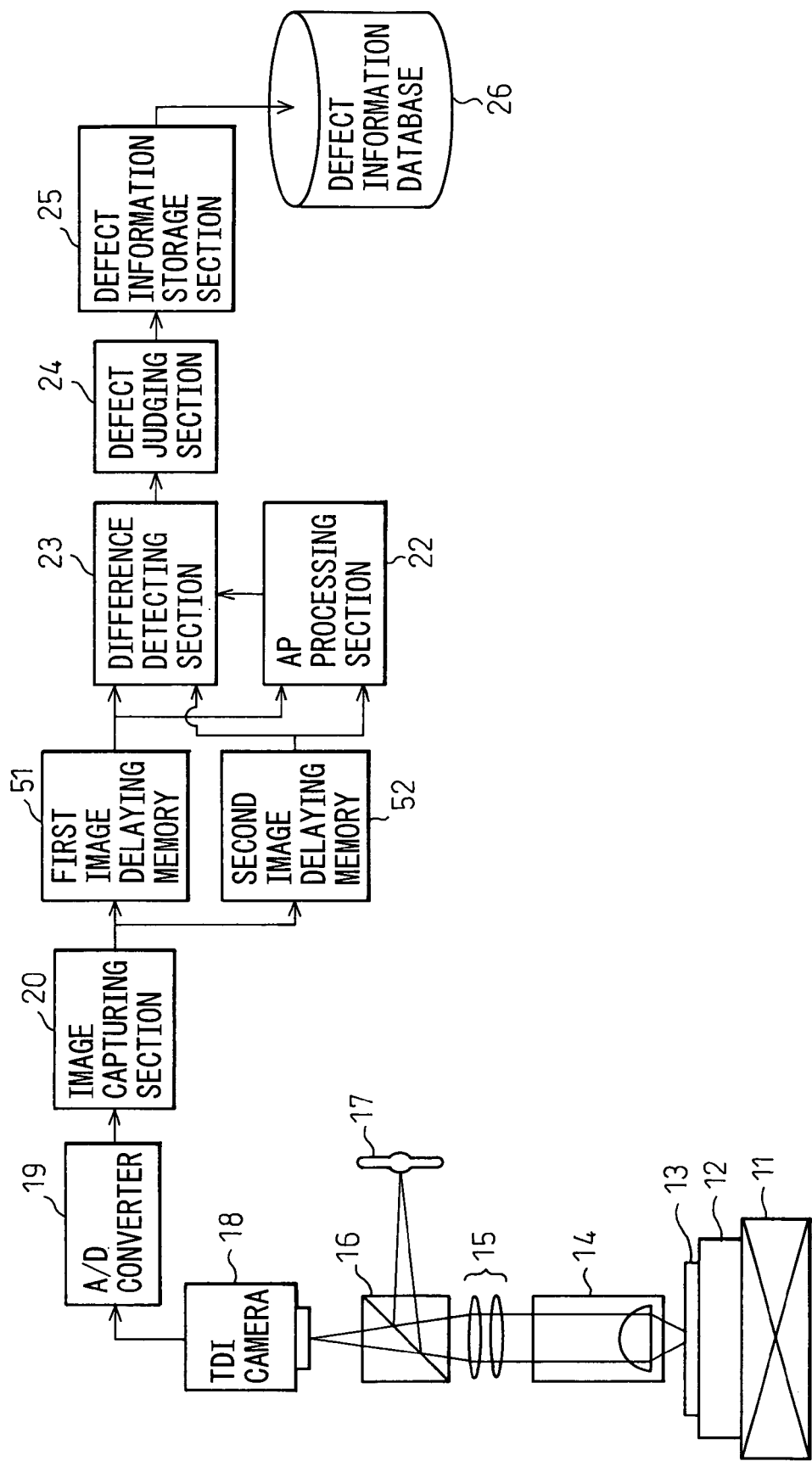
FIG. 8 is a diagram showing the configuration of a die comparison section in a pattern inspection apparatus in a first embodiment of the present invention.

FIG. 8 is a diagram showing the configuration of the die comparison section in the pattern inspection apparatus (inspection machine of a semiconductor wafer) in the first embodiment of the present invention. As obvious, by comparison with the conventional apparatus shown in FIG. 4, the present pattern inspection apparatus differs from that shown in FIG. 4 in that a first image delaying memory 51 and a second image delaying memory 52 are provided instead of the image delaying memory 21, and that the AP processing section 22 detects a positional deviation based on the images equivalent to two dies stored in the first image delaying memory 51 and the second image delaying memory 52 and calculates the quantity of correction based on the data of the positional deviations at multiple separate places. The first image delaying memory 51 has a capacity for images equivalent to at least two dies, the second image delaying memory 52 has a capacity for images equivalent to at least one die, and after being written to the capacity limit, the memories are overwritten sequentially. The configuration shown in FIG. 8 can be realized by the processing unit shown in FIG. 5 and if the processor has a sufficient processing ability, it is desirable that an image memory 32 has a capacity equivalent to at least two dies and writing from the image capturing section 20 and accessing of a processor 34 can be carried out in parallel. In the pattern inspection apparatus in the first embodiment, the cell comparison is carried out in parallel and a cell comparison processing section having a configuration similar to a conventional one is provided separately, though not shown here.

Figure 9:
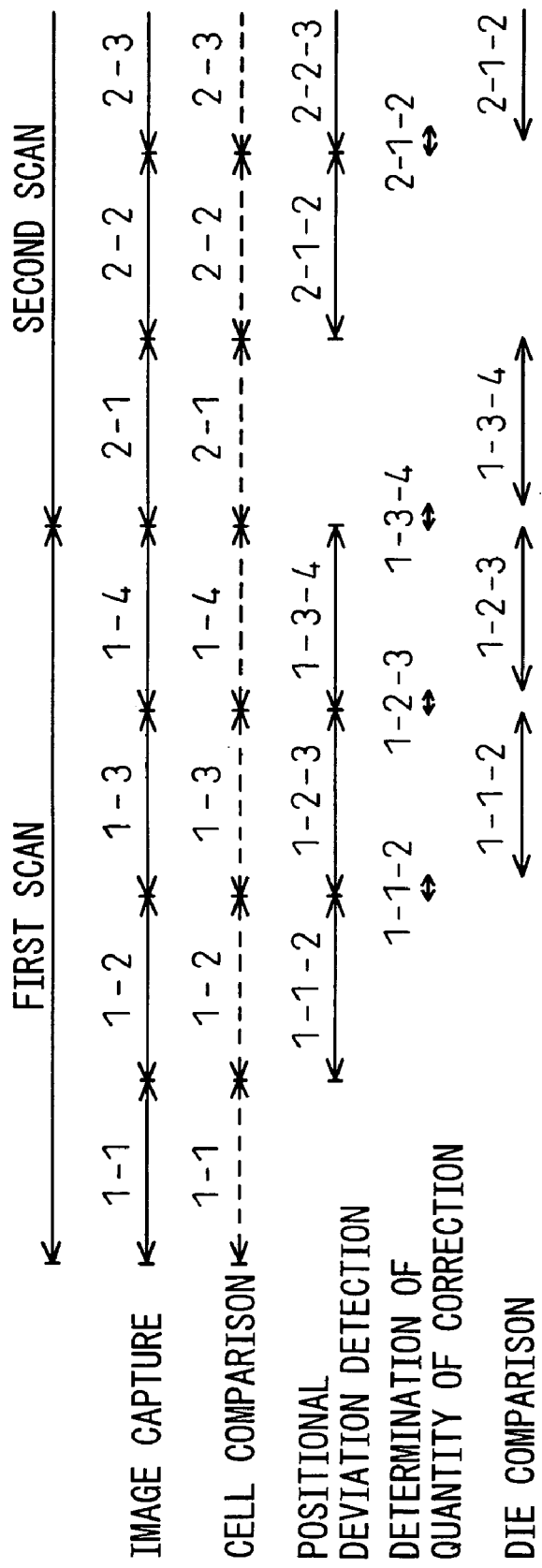
FIG. 9 is a time chart showing the action of each part in the pattern inspection apparatus in the first embodiment.

FIG. 9 is a time chart showing the relationship of process of each part in the pattern inspection apparatus in the first embodiment. As shown schematically, the images of the individual dies are captured and stored one after another during scanning and the cell comparison processing section carries out the cell comparison sequentially when two cell patterns are captured. Therefore, the cell comparison of each die is completed at the same time the image capture of each die is completed. When the image capture of a first die 1-1

(scan of a first die) in the first row is completed and the image capture of a second die 1-2 (scan of a second die) is started, the detection of positional deviation between the first die 1-1 and the second die 1-2 is started sequentially for each frame, and the detection of positional deviation between frames is completed at the time the image capture of the second die 1-2 (scan of the second die) is completed. At this time, the cell comparison of the second die 1-2 is also completed.

Next, when the image capture of a third die 1-3 (scan of a third die) in the first row is started, the quantity of positional deviation correction between the first die 1-1 and the second die 1-2 is determined based on the positional deviations detected in all of the frames between the first die 1-1 and the second die 1-2, and after correction by a quantity corresponding to the quantity of correction is made, the die comparison is made. In this example, the time required for making the die comparison is shorter than the time required for scanning one die, and when the image capture of the third die 1-3 is completed, the die comparison between the first die 1-1 and the second die 1-2 is already completed. When the image capture of the third die 1-3 is completed, the cell comparison of the third die 1-3 and the detection of positional deviation between the second die 1-2 and the third die 1-3 are already completed.

The above-mentioned processes are carried out sequentially and when the first scan is completed, the image capture of the last die in the row (a fourth die 1-4, here), the cell comparison and the detection of positional deviation are already completed, and when the scan of the first die in the next row (a first die 2-1 in the second row, here) is completed, the die comparison between the second last die (the third die 1-3) and the last die (the fourth die 1-4) in the first row is completed. In the case of the scan shown in FIG. 2, the next row is scanned in the opposite direction. The double detection cannot be carried out for the dies at both ends, therefore, the above-mentioned process is carried out separately.

Figure 10:
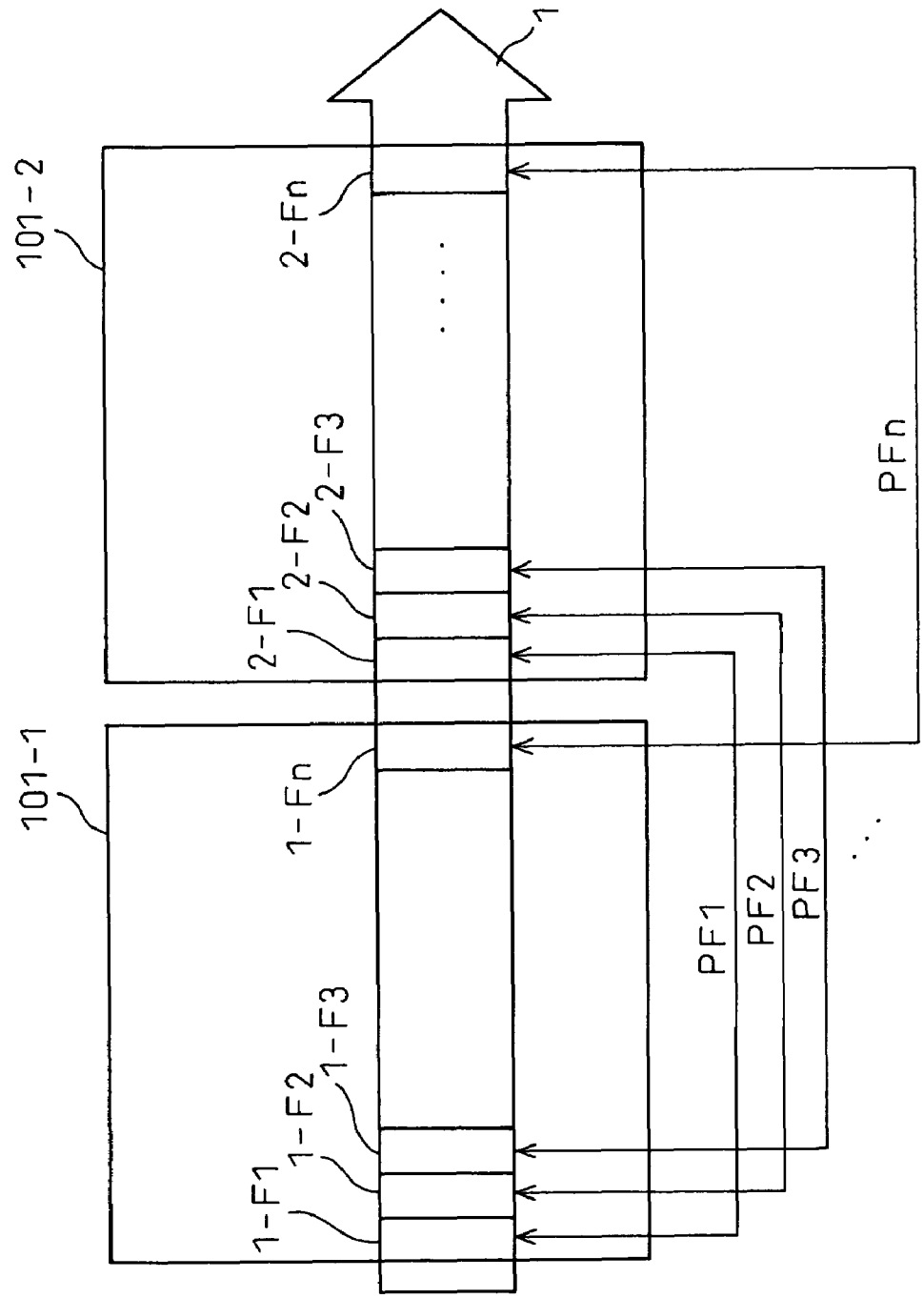
FIG. 10 is a diagram for explaining the positional deviation detection in the pattern inspection apparatus in the first embodiment.

FIG. 10 is a diagram for explaining the detection of positional deviation in the AP processing section 22 in the first embodiment. The positional deviation for each frame is detected by comparing the images of the two dies 101-1 and 101-2 to be compared on a frame basis. For example, first the patterns in the frame 1-F1 in the first die 101-1 and the frame 2-F1 in the second die 101-2 are compared to detect a positional deviation PF1, then patterns in the frame 1-F2 in the first die 101-1 and the frame 2-F2 in the second die 101-2 are compared, and thus positional deviations PF2, PF3, . . . , PFn (n denotes the number of frames) of all the rest of the frames in the two dies 101-1 and 101-2 are detected. After this, the positional deviations PF1, PF2, PF3, . . . , PFn are plotted according to the position of the frame and an expression of a line showing the positional deviation is calculated by the least squares method. The quantity of positional deviation is obtained in two directions, that is, the X direction and the Y direction. The quantity of correction is calculated based on the above-mentioned expression for each frame in accordance with the position thereof.

The difference detecting section 23 detects a difference for each pixel after the positional alignment correction is carried out by correcting one of the image positions by the quantity of correction calculated for each frame. In the same manner as that in the conventional case, the defect detecting section 24 judges whether the difference is equal to or greater than the threshold value and stores it as a defect candidate in the defect information storage section 25 when the difference is equal to or greater than the threshold value.

A pixel judged to be a defect candidate by the die comparison and the cell comparison is stored in a defect information database 26.

There can be obtained various examples of modifications for the positional deviation detection and correction. For example, in the first embodiment, the positional deviations PF1, PF2, PF3, . . . , PFn in all of the frames are utilized for calculating the quantity of correction, but it is also possible to utilize only the quantity of positional deviation in frames where there is a remarkable coincidence. When the quantity of positional deviation in each frame is calculated, one image is moved to calculate the degree of coincidence and the quantity of positional deviation is obtained as the quantity of movement when the degree of coincide becomes maximum, but if there is a difference between two images due to variations in color or if a defect exists, the degree of coincidence is lowered. The precision of correction can be improved by excluding the quantity of positional deviation in frames where there is a poor coincidence from the calculation of the quantity of correction.

Moreover, when there are a small number of patterns which can be used for the detection of positional deviation in a frame, the precision of correction can be improved by excluding the quantity of positional deviation in the frame where there are a small number of patterns from the calculation of the quantity of correction, because in such a case, the precision of the detection of the quantity of positional deviation is degraded.

It is also desirable that the quantity of positional deviation in a frame, which differs considerably from the quantity of positional deviation in other frames is excluded from the calculation of the quantity of correction.

Moreover, because the same mask pattern is exposed to each die by the use of a stepper or the like and the moving mechanism of a stage in a pattern inspection apparatus is highly precise, it can be thought that the positional deviation between the captured images of two dies is the same all over the dies. In other words, it is thought that the two images are in a relationship in which one of the dies, as a whole, has been translated or rotated, that is, the two images are in a relationship after a linear coordinate transformation has been conducted, therefore, it is possible to calculate the positional deviation for the entire die if there are data on the positional deviation, at least, at two places. From this it follows that it is not necessary to detect the positional deviation for each frame as in the first embodiment, and it is also possible to calculate the quantity of correction for each frame by, for example, detecting the positional deviation in multiple frames having a large number of patterns and by calculating the positional deviation for the entire die. Due to this, it is possible to considerably reduce the amount of operations required for detecting the positional deviation.

Next, a pattern inspection apparatus in a second embodiment of the present invention will be explained below. The die comparison processing section in the pattern inspection apparatus in the second embodiment has a configuration similar to that in the first embodiment shown in FIG. 8, but differs in that the first image delaying memory 51 and the second image delaying memory 52 have a capacity for storing images at least within the scan width in a row, that is, for storing images of multiple dies, and that the AP processing section 22 carries out the detection of positional deviation between images of neighboring dies as in the first embodiment and, at the same time, determines the quantity of correction based on information containing the relative position of images of multiple dies separated from each another in a row in the scanning direction in the arrangement of dies. The cell comparison processing section is also provided in the pattern inspection apparatus in the second embodiment, and the configuration thereof is the same as that of the first embodiment (that is, the conventional case).

Figure 11:
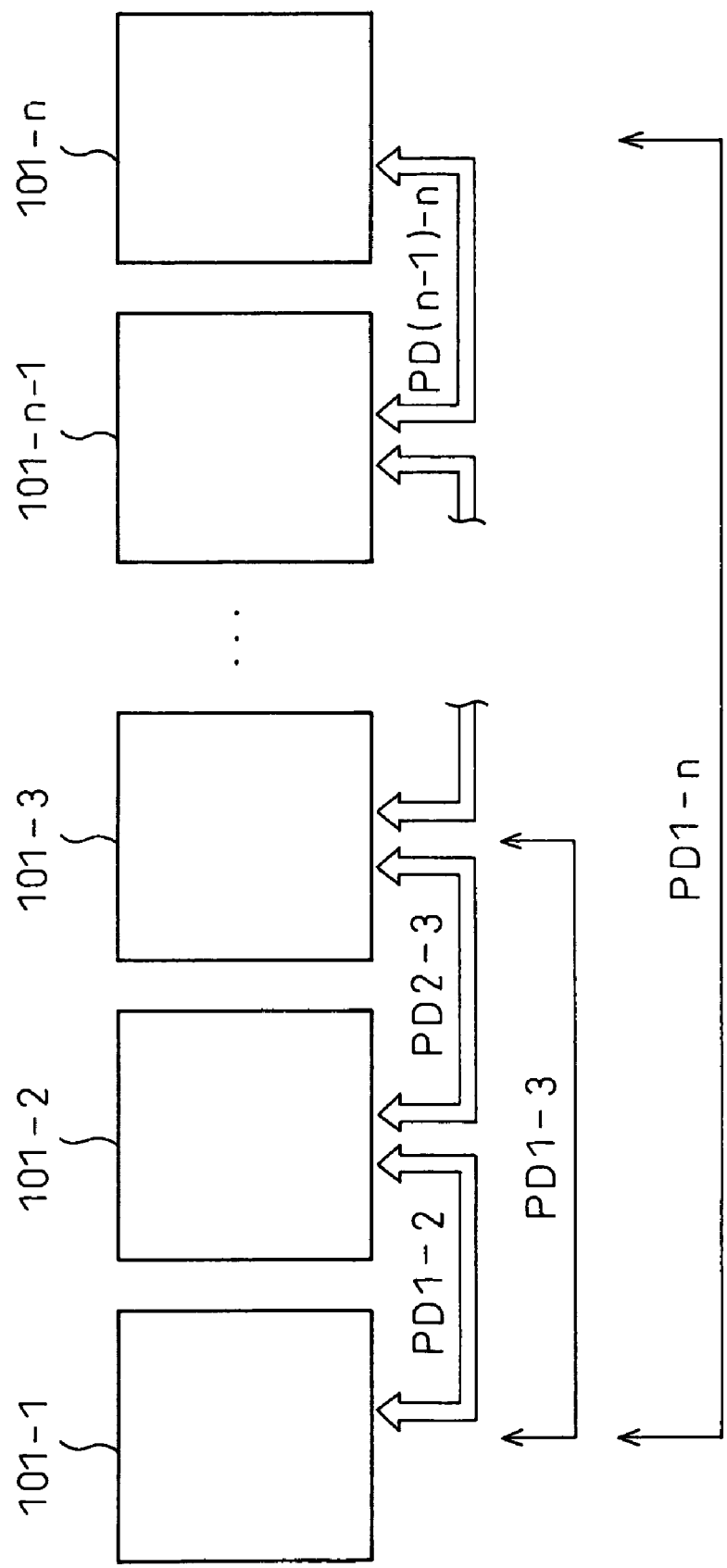
FIG. 11 is a diagram for explaining the positional deviation detection in a pattern inspection apparatus in a second embodiment of the present invention.

FIG. 11 is a diagram for explaining the process of the determination of the quantity of correction in the AP processing section 22 in the second embodiment. In FIG. 11, reference numbers 101-1 to 101-n denote dies or images thereof in a row. As in the first embodiment, quantities of positional deviation PD1-2 to PD(n-1)-n are detected at multiple places between images of neighboring dies. In the second embodiment, a quantity of positional deviation PD1-3 between the first die and the third die or a quantity of positional deviation PF1-n between the first die and the last die, that is, the n-th die, two dies not being adjacent to each other, is further detected and the quantity of correction of positional deviation of dies in the row is determined by utilizing these quantities. The quantity of positional deviation between dies which are not adjacent to each other can be obtained from the quantities of positional deviation between neighboring dies PD1-2 to PD(n-1)-n, but it is also possible to detect the positional deviation by comparing patterns of dies which are not adjacent to each other.

Each die is exposed while a stepper or the like shifts the exposure position. The moving mechanism of an exposure apparatus, such as a stepper, is very highly precise and each die is formed into a regular arrangement on a wafer. The moving mechanism of a pattern inspection apparatus is also very highly precise and if the arrangement position of dies on the wafer is viewed in terms of the coordinates of the moving mechanism of a pattern inspection apparatus, it is possible to regard that the coordinates are transformed linearly. Therefore, if the quantity of correction is determined based on information of the relative positions (positional deviation information) of the images of multiple separate dies (patterns) in a row, as in the second embodiment of the present invention, the positional deviation can be corrected more precisely.

Figure 12:
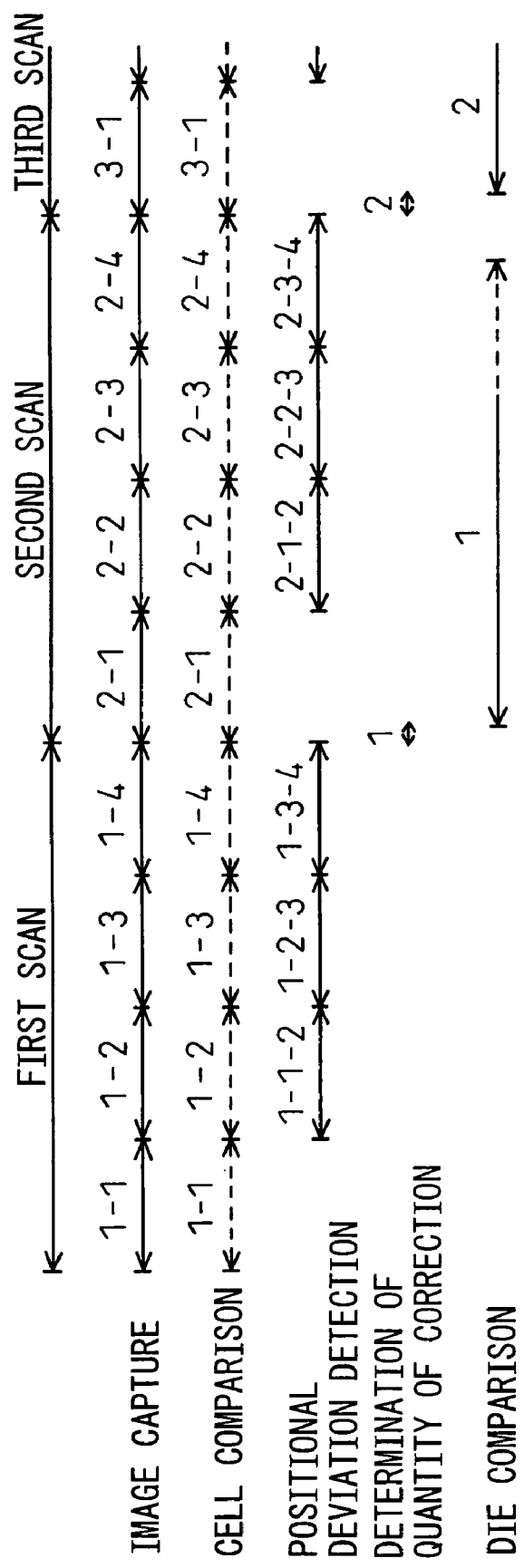
FIG. 12 is a time chart showing the action of each part in the pattern inspection apparatus in the second embodiment.

FIG. 12 is a time chart showing the relationship of process of each part in the pattern inspection apparatus in the second embodiment. As shown schematically, the image of each die is captured and stored sequentially during scanning and the cell comparison is made sequentially when two cell patterns are captured for comparison at the cell part. Therefore, the cell comparison of each die is completed at the time the image capture of each die is completed. When the image capture of the first die 1-1 (scan of the first die) in the first row is completed and the image capture of the second die 1-2 (scan of the second die) is started, the detection of positional deviation between the first die 1-1 and the second die 1-2 is started sequentially for each frame, and when the image capture of the second die 1-2 (scan of the second die) is completed, the detection of positional deviation between frames is already completed. At this time, the cell comparison of the second die 1-2 also is completed already. The process as described above is repeated and the images of the four dies in the first row are captured, the cell comparison is made, and the positional deviation between the third and the fourth dies is detected.

At the time when the positional deviation between the third and the fourth dies in the first row is detected, the quantity of correction for positional deviation between dies in the first row is determined based on the quantities of positional deviation including the quantities of positional deviation between dies which are not adjacent to each other in the first row, and after correction is made based on the quantity of correction, the die comparison is made for the dies in the first row.

When the image capture of the four dies in the first row and the cell comparison are completed, the image capture, the cell comparison, and the detection of the quantity of positional deviation between neighboring dies are started for the dies 2-1 to 2-4 in the second row in the same manner as described above. As a result, the determination of the quantity of positional deviation and the die comparison in the first row are carried out in parallel to the image capture of dies in the second row, the cell comparison, and the detection of positional deviation between neighboring dies. In this example, the comparison process of all the dies in the first row is completed during the image capture of dies in the first row.

In the second embodiment, the die comparison process of all the dies in the first row is completed during the image capture of the dies in the next row. This requires for the processing unit to be capable of carrying out the image capture of dies, cell comparison, detection of positional deviation, determination of the quantity of correction and die comparison of at least one row during scanning of dies of the row. A pattern inspection apparatus in a third embodiment is suitable to a case where the processing ability of a processing unit is not sufficient and the above-mentioned demand cannot be met.

Figure 5:
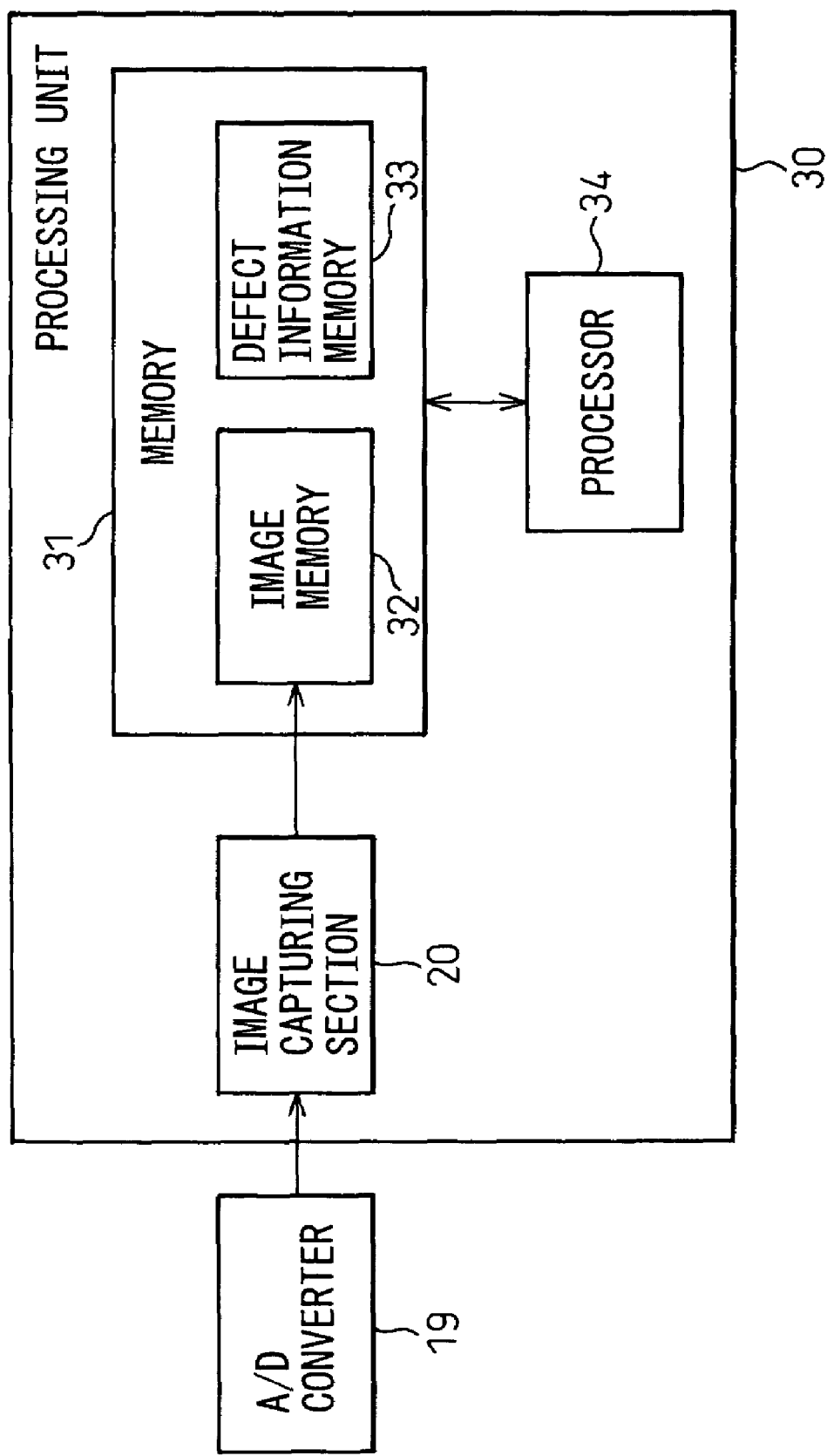
FIG. 5 is a diagram showing the configuration when a processing unit is realized by a processor and a memory.
Figure 7:
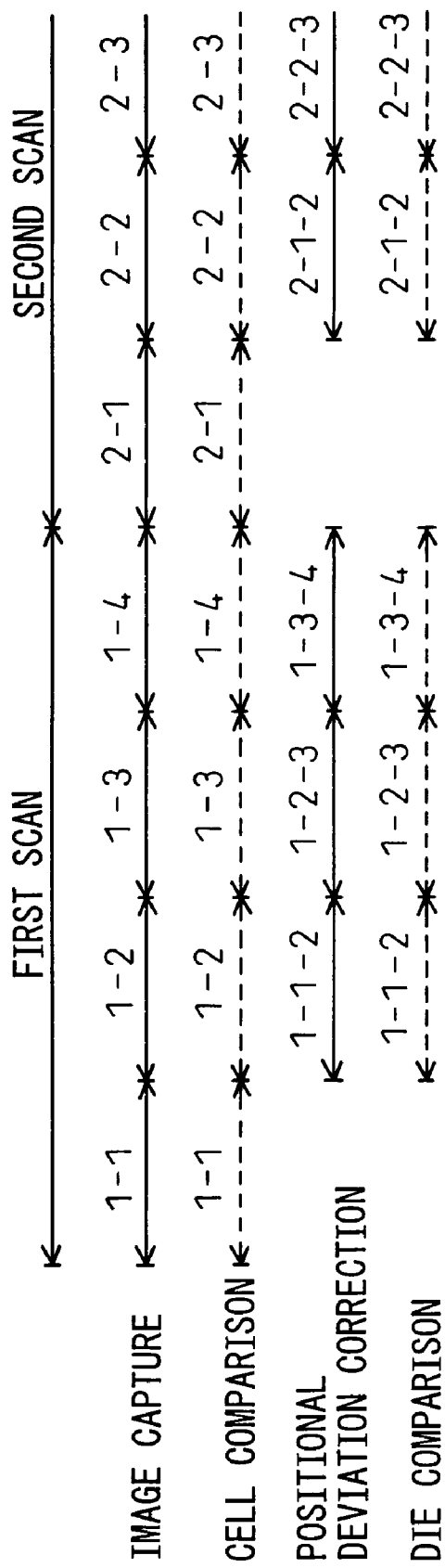
FIG. 7 is a time chart showing the action of each part in a configuration disclosed publicly, in which the die comparison inspection and the cell comparison inspection are made in separate circuits, respectively.
Figure 13A:
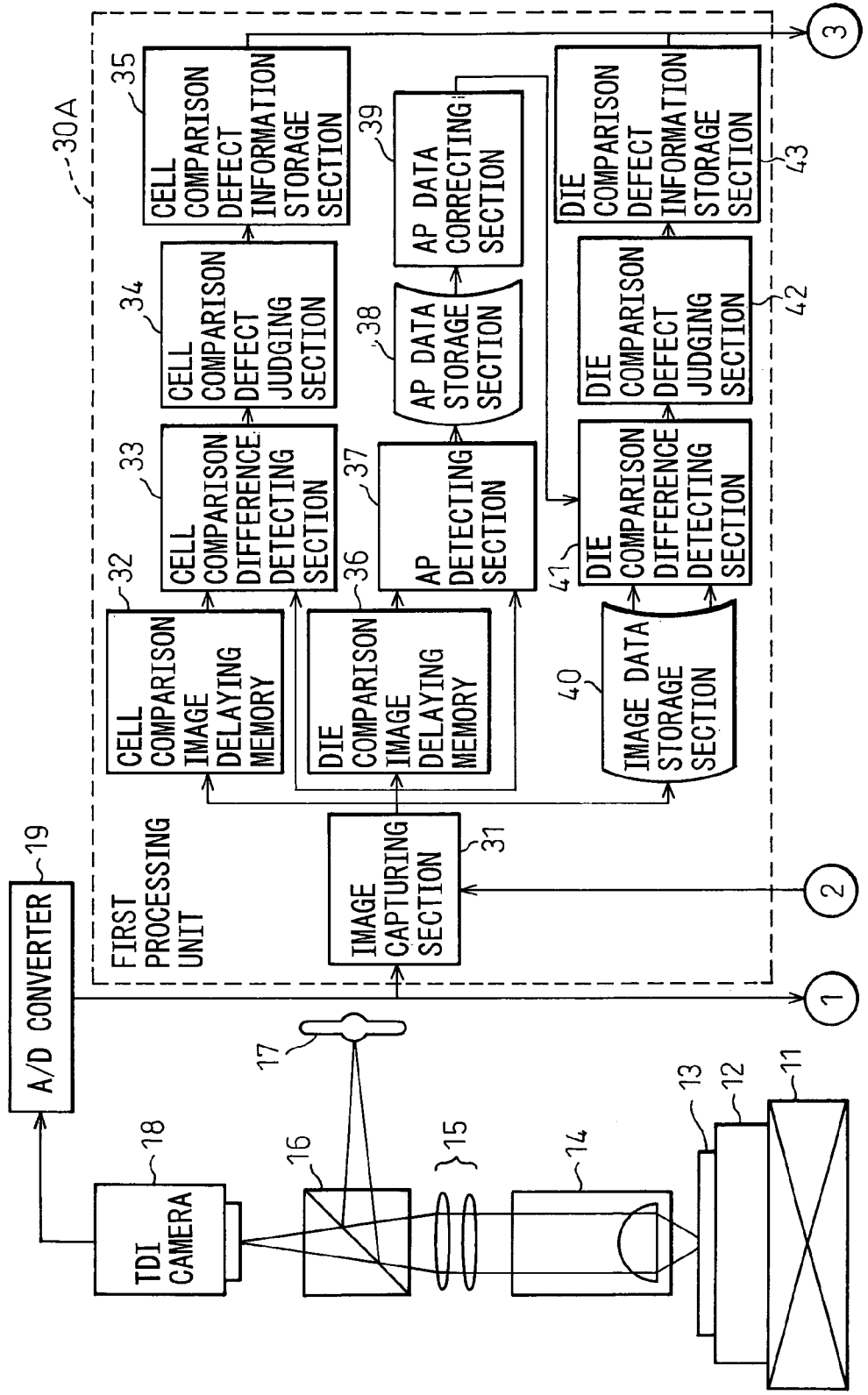
FIGS. 13A and 13B are diagrams showing the configuration of a pattern inspection apparatus in a third embodiment of the present invention.
Figure 13B:
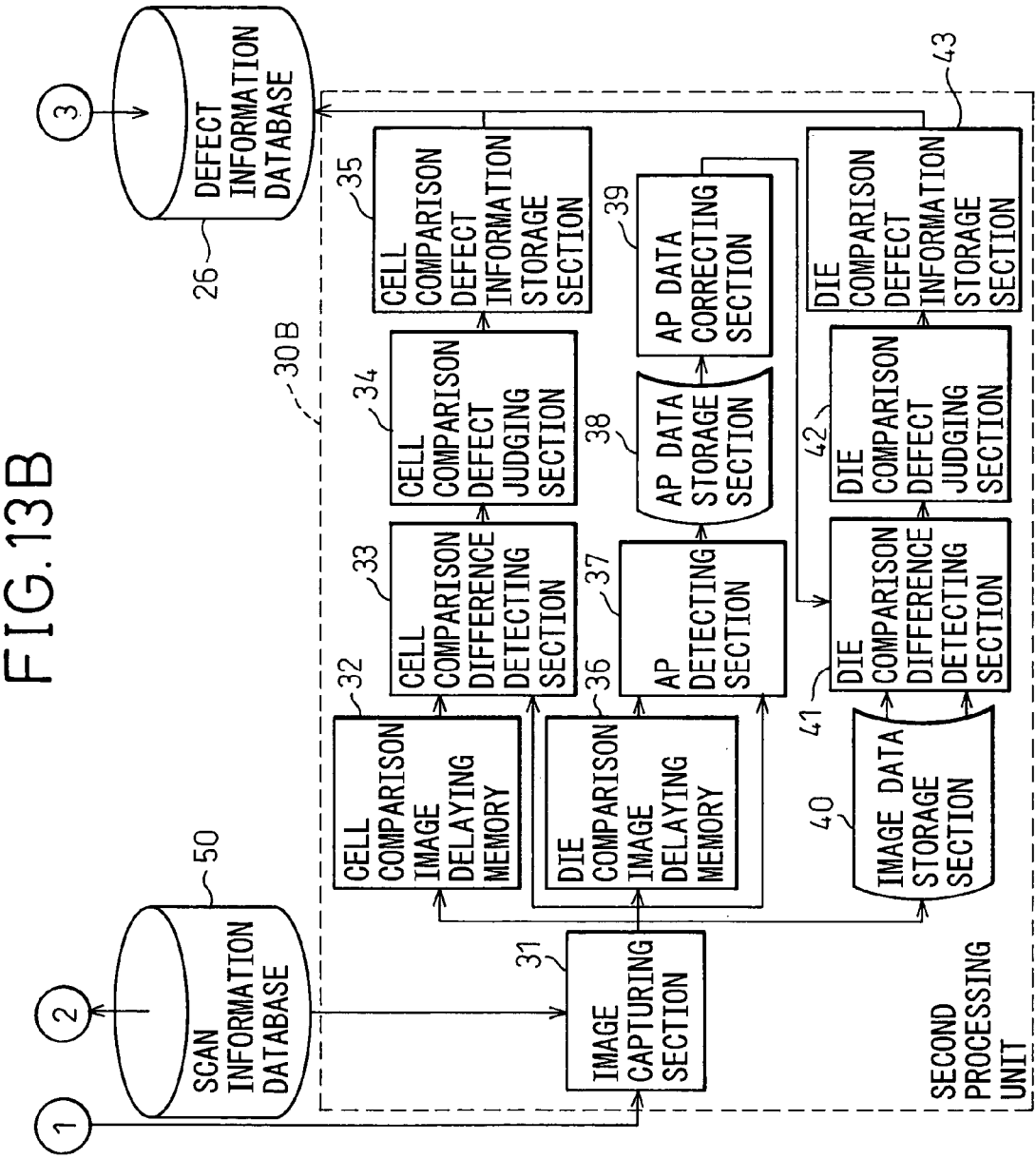

FIGS. 13A and 13B are diagrams showing the configuration of the pattern inspection apparatus in the third embodiment. As shown in FIGS. 13A and 13B, the inspection apparatus in the third embodiment has the same configuration as that of the second embodiment regarding the image capturing section and the A/D converter 19, but differs in having two processing units 30A and 30B. The processing units 30A and 30B have the same configuration and take turns to carry out, for each row, the storage of images, the cell comparison and detection of positional deviation, and the correction of positional relation and pattern comparison. Each processing unit can be realized by the use of hardware, for example, by the use of a processor and memory as shown in FIG. 5.

The image data of the cell part from the A/D converter 19 is stored in the cell comparison image delaying memory 32, and the image data of the peripheral circuit part or the data of all the images from the A/D converter 19 is stored in a die comparison image delaying memory 36 and an image data storage section 40 via the image capturing section based on the information about the peripheral circuit part and the cell part stored in a scan information database 50. The image capturing section 31 of the processing unit 30A captures, for example, the image data of dies in an odd-numbered row, and the image capturing section 31 of the processing unit 30B captures the image data of dies in an even-numbered row.

First, the cell comparison process is explained below. A cell comparison difference detecting section 33 synchronously reads the image data of the cell part from the image capturing section 31 and the image data delayed by an amount equivalent to one cell pattern period in a cell comparison image delaying memory 32, compares the gray level between the pixels corresponding to each other of the two images, and creates a gray level difference image. A cell comparison judging section 34 judges a pixel to be a defect candidate, which has a gray level difference exceeding a predetermined threshold for the gray level difference image created in the cell comparison difference detecting section 33. The detected defect candidate information is sent to a cell comparison information storage section 35. At this stage, it is not possible to judge which one of the cells, between which the comparison has been made, has the detected defect because the inspection is based on the single detection, but the defect inspection based on the double detection is made by overlapping the results of the comparison between cells, which is made after the single detection in the same manner, between successive cells, and the detected defect information is stored in the defect information database.

Next, the positional deviation detection and correction of the die comparison process are explained below. The die comparison image delaying memory 36 temporarily stores the image corresponding to one die and sends the image to an AP detecting section 37 after delaying the timing thereof by an amount equivalent to one die. The AP detecting section 37 synchronously reads the image delayed by an amount equivalent to one die in the die comparison image delaying memory 36 and the image data from the image capturing section 31, obtains the quantity of positional deviation between the two images, and stores the quantity in an AP data storage section 38. The AP data storage section 38 stores the quantities of positional deviations between neighboring dies in a row. An AP data correcting section 39 corrects the data, the reliability of which is poor and which seems to have failed in detecting the positional deviation among the data of the quantities of positional deviations in a row stored in the AP data storage section 38, by the use of data in the vicinity thereof and the reliability of which is higher, and determines the quantity of correction of positional deviation for the entire row.

Next, the die comparison process is explained below. A die comparison difference detecting section 41 reads images of two neighboring dies from the image data storage section 40 and, after carrying out the positional alignment of the two images based on the quantity of correction of positional deviation determined by the AP data correcting section 39, makes a comparison of the gray level between pixels corresponding to each other and creates a gray level difference image. A die comparison defect judging section 42 judges a pixel to be a defect candidate, which has a gray level difference exceeding a predetermined threshold for the gray level difference image created in the cell comparison difference detecting section 41. It is desirable to set the threshold in this case to one greater than that in the case of the cell comparison process in order to prevent unwanted detection of a defect. Information of the detected defect candidate is sent to a die comparison defect information storage section 43 and stored therein. In this case also, the inspection is based on the single detection, therefore, the inspection based on the double detection is made in the same manner described above and, when the defect exists at the same place, it is judged to be a defect and stored in the defect information database 26.

FIG. 14 is a time chart showing the action of each part of the pattern inspection apparatus in the third embodiment. During the first scan, as shown schematically, in the first processing unit 30A, the part relating to the image capturing process for capturing images into the cell comparison image delaying memory 32, the die comparison image delaying memory 36 and the image data storage section 40, and relating to the cell comparison (the cell comparison image delaying memory 32, the cell comparison difference detecting section 33, the cell comparison defect judging section 34 and the cell comparison defect information storage section 35) carries out the cell comparison process, and the part relating to the detection of positional deviation for the die comparison (the die comparison image delaying memory 36, the AP detecting section 37 and the AP data storage section 38) carries out the positional deviation detecting process. In the meantime, the AP data correcting section 39 and the part relating to the die comparison (the image data storage section 40, the die comparison difference detecting section 41, the die comparison defect judging section 42 and the die comparison defect information storage section 43) in the first processing unit 30A is placed in a standby condition without doing any action. Moreover, each part in the second processing unit 30B is also placed in a standby condition without doing any action.

Next, when the second scan is carried out in the opposite direction, the AP data correcting section 39 in the first processing unit 30A determines the quantity of correction of positional deviation during the first scan and, in accordance with this, the part relating to the die comparison makes the die comparison. At the same time, the part relating to the image capturing process for capturing images into the cell comparison image delaying memory 32, the die comparison image delaying memory 36 and the image data storage section 40, and relating to the cell comparison in the second processing unit 30B carries out the cell comparison process, and the part relating to the detection of positional deviation for die comparison carries out the positional deviation detecting process.

Subsequently to this, during odd-numbered scans, the first processing unit 30A carries out the image capturing process, the cell comparison process and the positional deviation detecting process for the part being scanned, and the second processing unit 30B carries out the determining process of the quantity of correction of positional deviation and the die comparison process for the part scanned before. During even-numbered scans, the first processing unit 30A carries out the determining process of the quantity of correction of positional deviation and the die comparison process for the part scanned before, and the second processing unit 30B carries out the image capturing process, the cell comparison process and the positional deviation detecting process for the part being scanned.

When the last scan is completed, the processing unit which has captured the last scanned image carries out the determining process of the quantity of positional deviation correction and the die comparison process, and thus all the inspections are completed.

In the third embodiment, it is assumed that the time required for the image capturing process, that for the determination of the quantity of correction for the die comparison, and that for the die comparison are substantially the same, but the die comparison requires many operations and there can be a case where the die comparison requires a longer processing time than the image capturing process. In other words, there can be a case where although the image capturing process, the cell comparison process and positional deviation detecting process for a certain row are completed, the determination of the quantity of correction for the die comparison for the previous row and the die comparison process are not completed yet. In this case, three or more processing units are provided and the process is carried out by using these units repeatedly by turns.

In the third embodiment, each processing unit has an image data storage section and the image data for each row to be used for the die comparison is stored in each processing unit. Therefore, in the process for the last row, it is necessary for the processing unit which has captured the image data of the row to carry out the process to the last and it is not possible for the other processing units, even if which have completed the processes and which are in a standby state, to carry out the process of the image data of the last row. In the above-mentioned case where the die comparison process requires a longer process time than the image capturing process, even if three or more processing units are provided and the process is carried out by turns, there arises a problem: a considerable period of time is required after the capture of the image of the last row (scan of the last row) is completed in order to complete all the processes. In the fourth embodiment, this problem is solved.

Figure 15:
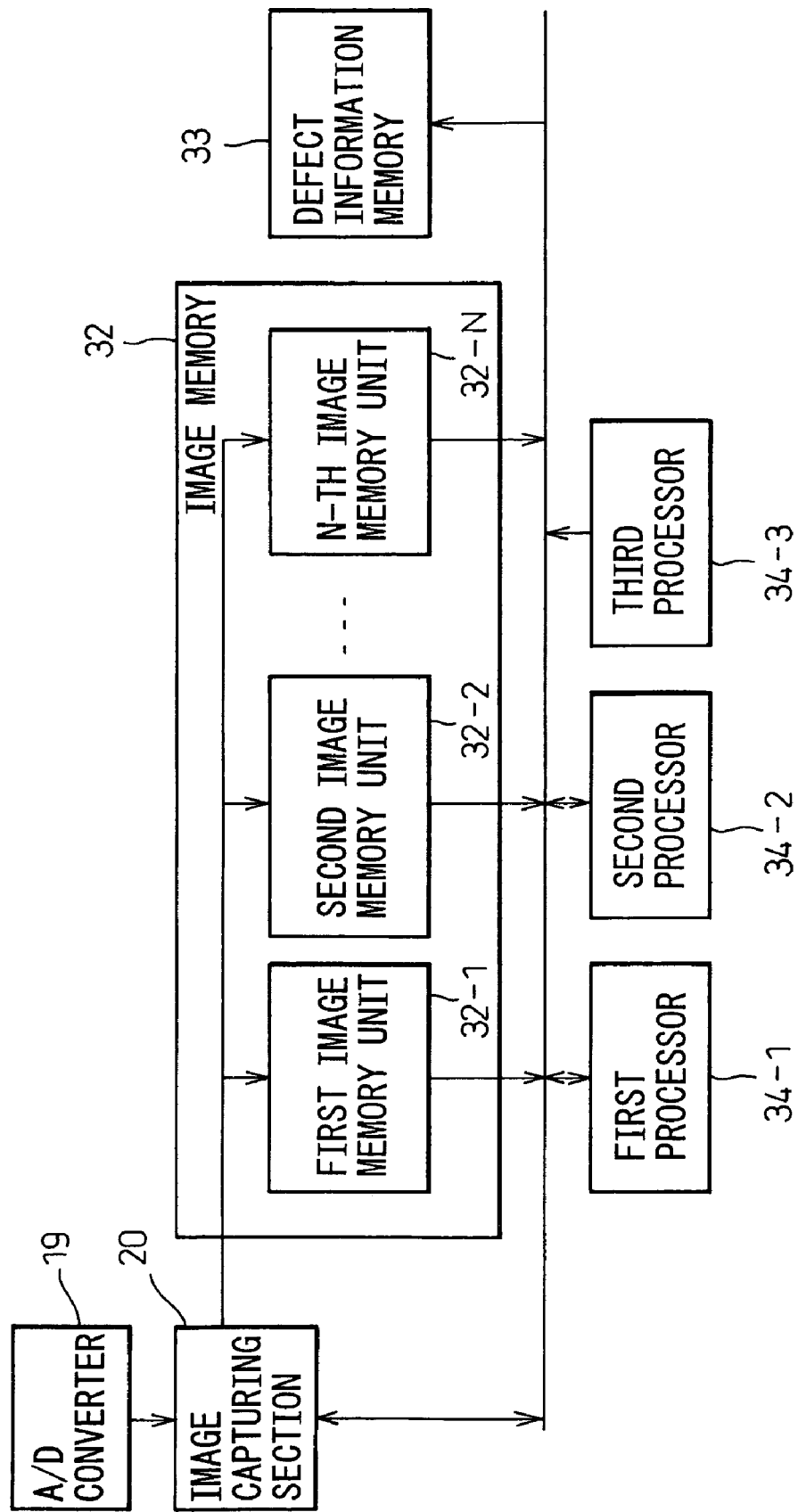
FIG. 15 is a diagram showing the configuration of a pattern inspection apparatus in a fourth embodiment of the present invention.

FIG. 15 is a diagram showing the configuration of the pattern inspection apparatus in the fourth embodiment of the present invention. As shown schematically, the pattern inspection apparatus in the fourth embodiment is realized by the use of multiple processors 34-1, 34-2 and 34-3 and memories. As shown schematically, the image memory 32 is made up of a plurality of memory units 32-1, 32-2, . . . , 32-N, and each memory is a shared memory which can be accessed freely from any processor. Moreover, the memory 33 for storing defect candidates can be accessed from each processor. The image data from the A/D converter 19 is stored sequentially in the plurality of memory units 32-1, 32-2, . . . , 32-N of the image memory 32 through the image capturing section 20, and after the data is stored in the last memory unit, the data is overwritten sequentially in the memory units starting again from the first memory unit. In this case, it is necessary for all of the processes of the image data stored in the memory units to be completed already before the memory units are overwritten, and the memory capacity is determined with this condition being taken into account. Each processor, when in a standby state, carries out the processes in a sharing manner by turns.

FIG. 16 is a time chart showing the processes in the fourth embodiment in an example where the time required for the determination of the quantity of correction for the die comparison and that for the die comparison process are longer than those required for the image capturing process, the cell comparison process and the positional deviation detecting process, but are shorter than twice as much.

First, the image capturing process of the first row is carried out and the data is stored in the first image memory unit 32-1, and at the same time the first processor 34-1 carries out the cell comparison process and the positional deviation detecting process of the first row (C1) based on the image data stored in the first image memory unit 32-1. Upon its completion, the first processor 34-1 and the third processor 34-3 carry out the determination of the quantity of correction for the die comparison and the die comparison based on the image data stored in the first image memory unit 32-1. For example, the processes are shared in such a way that the first processor 34-1 carries out the comparison process for the dies in the front half of the first row (D1F) and the third processor 34-3 carries out the comparison process for the dies in the rear half of the first row (D1R).

When the image capturing process of the first row is completed and the die comparison of the first row is started, the image capturing process of the second row is started and the data is stored in the second memory unit 32-2, and at the same time the second processor 34-2 carries out the cell comparison process and the positional deviation detecting process of the second row (C2) based on the image data stored in the second image memory unit 32-2. In other words, the processes C2, D1F and D1R are carried out in parallel.

Upon completion of the image capturing process of the second row, the second processor 34-2 and the first processor 34-1 carry out the determination of the quantity of correction for the die comparison and the die comparison based on the image data stored in the second image memory unit 32-2. For example, the processes are shared in such a way that the second processor 34-2 carries out the comparison process for the dies in the front half of the second row (D2F) and the first processor 34-1 carries out the comparison process for the dies in the rear half of the second row (D2R).

When the image capturing process of the second row is completed and the die comparison of the second row is started, the image capturing process of the third row is started and the data is stored in the third image memory unit 32-2, and at the same time the third processor 34-3 carries out the cell comparison process and the positional deviation detecting process (C3) based on the image data stored in the third image memory unit 32-3. In other words, the processes C3, D2F and D2R are carried out in parallel.

Subsequently to this, the processes described above are repeated. Regarding the last row, the image capturing process of the last row is started and another processor carries out the cell comparison process and the positional deviation detecting process (C3) of the last row. When the image capturing process of the last row is completed, the processor and another processor carry out the die comparison process of the last row in a sharing manner.

The example where three processor are used is described as above. When the time required for the determination of the quantity of correction for die comparison and the die comparison process is m times that required for the image capturing process, that is, the time required for the scan of one row, the cell comparison process, the positional deviation detecting process, the determination of the quantity of correction and the die comparison process can be carried out by each processor in a properly sharing manner by using (m+1) processors each time the image capturing process is carried out.

Although the embodiments of the present invention are described as above, there can be obtained various modifications of the present invention. For example, the position is corrected based on the relative position of the images to be compared in the description made above, but it is also possible to use absolute coordinates with a specific point of a wafer or a die being the origin. Moreover, it is possible to provide multiple processors in order to carry out the processes in a sharing manner as shown in FIG. 15 in the first embodiment.

According to the present invention, as described above, it is possible to improve the precision of the detection of positional deviation and the correction of images which are the objects of the die comparison, and as a result, improve the detection precision of a pattern inspection method and a pattern inspection apparatus. Moreover, with the improved detection precision, it is possible to effectively carry out both the die comparison and the cell comparison.

We claim:

1. A pattern inspection method comprising:
    capturing images, by scanning an object to be inspected on which a plurality of identical patterns are arranged, of the plurality of the identical patterns;
    detecting positional information of the images of neighboring identical patterns;
    determining a quantity of correction, by which a positional relation of the images of the neighboring identical patterns is corrected, based on the detected positional information; and
    comparing the images the positional relation of which has been corrected based on the quantity of correction, wherein the quantity of correction is determined based on the positional information of the images at multiple separate places in the pattern, wherein the detection of the positional information of the images, the determination of the quantity of correction and the comparison of the images are carried out in parallel with the scan for capturing the images to be used for a subsequent comparison, and wherein the determination of the quantity of correction and the comparison of the images are started after the capture of the images of two of the neighboring patterns is completed.

2. A pattern inspection method comprising:

capturing images, by scanning an object to be inspected on which a plurality of identical patterns are arranged, of the plurality of the identical patterns;

detecting positional information of the images of neighboring identical patterns;

determining a quantity of correction, by which a positional relation of the images of the neighboring identical patterns is corrected, based on the detected positional information; and comparing the images the positional relation of which has been corrected based on the quantity of correction, wherein the quantity of correction is determined based on the positional information of the images at multiple separate places in the pattern, wherein the detection of the positional information, the determination of the quantity of correction and the comparison of the images are carried out in parallel with the scan for capturing the images to be used for a subsequent comparison, and wherein the determination of the quantity of correction and the comparison of the images are started after the capture of the images of the patterns in each row is completed.

3. A pattern inspection method comprising:

capturing images, by scanning an object to be inspected on which a plurality of identical patterns are arranged, of the plurality of the identical patterns;

detecting positional information of the images of neighboring identical patterns;

determining a quantity of correction, by which a positional relation of the images of the neighboring identical patterns is corrected, based on the detected positional information; and comparing the images the positional relation of which has been corrected based on the quantity of correction, wherein the quantity of correction is determined based on the positional information of the images at multiple separate places in the pattern, wherein each pattern has a cell pattern repeated at a predetermined pitch, and wherein a cell comparison for comparing the neighboring cell patterns in each pattern is made immediately after the capture of the images of the neighboring cell patterns and in parallel to the capture of the images to be used for a subsequent cell comparison.

4. A pattern inspection apparatus comprising:

an image capturing section for capturing images, by scanning an object to be inspected on which a plurality of identical patterns are arranged, of the plurality of the identical patterns;

an image storage section for storing the captured images;

a positional information detecting section for detecting positional information of the images of neighboring identical patterns;

a correction quantity determining section for determining a quantity of correction, by which a positional relation of the images of the neighboring identical patterns is corrected, based on the detected positional information; and a pattern comparison section for correcting the positional relation based on the quantity of correction and comparing the corrected images, wherein the correction quantity determining section determines the quantity of correction based on the positional information of the images at multiple separate places in the pattern, wherein the detection of the positional information of the image by the positional information detecting section, the determination of the quantity of correction by the correction quantity determining section and the comparison of the images by the pattern comparison section are carried out in parallel to the capture of the images to be used for a subsequent comparison by the image capturing section and the storage of the images, and wherein the image storage section has a capacity for storing images of at least two patterns, and after the capture of two neighboring images by the image capturing section and the storage of the images are completed, the correction quantity determining section and the pattern comparison section start the determination of the quantity of correction and the comparison of the images.

5. A pattern inspection apparatus comprising:

an image capturing section for capturing images, by scanning an object to be inspected on which a plurality of identical patterns are arranged, of the plurality of the identical patterns;

an image storage section for storing the captured images;

a positional information detecting section for detecting the positional information of the images of the identical patterns in each row;

a correction quantity determining section for determining a quantity of correction, by which the positional relation of the images of the neighboring patterns is corrected, based on the detected positional information; and a pattern comparison section for correcting the positional relation based on the quantity of correction and comparing the corrected images, wherein the correction quantity determining section determines the quantity of correction based on the positional information of the images at multiple separate places in each row in the scanning direction in the pattern arrangement, wherein the detection of the positional information of the image by the positional information detecting section, the determination of the quantity of correction and the comparison of the images by the pattern comparison section are carried out in parallel to the capture of the images to be used for a subsequent comparison by the image capturing section and the storage of the images, and wherein the image storage section has a capacity for storing pattern images of at least one row, and after the capture of the pattern images of each row by the image capturing section and the storage of the images are completed, the correction quantity determining section and the pattern comparison section start the determination of the quantity of correction and the comparison of the images.

6. A pattern inspection apparatus comprising:

an image capturing section for capturing images, by scanning an object to be inspected on which a plurality of identical patterns are arranged, of the plurality of the identical patterns;

an image storage section for storing the captured images;

a positional information detecting section for detecting positional information of the images of neighboring identical patterns;

a correction quantity determining section for determining a quantity of correction, by which a positional relation of the images of the neighboring identical patterns is corrected, based on the detected positional information; and a pattern comparison section for correcting the positional relation based on the quantity of correction and comparing the corrected images, wherein the correction quantity determining section determines the quantity of correction based on the positional information of the images at multiple separate places in the pattern, wherein each pattern has a cell pattern to be repeated at a predetermined pitch, wherein a cell comparison section for making a comparison between the neighboring cell patterns in each pattern is included, and wherein the cell comparison section makes a comparison between the neighboring cell patterns in parallel to the capture of the images to be used for a subsequent comparison after the capture of the cell pattern images, which are the object for an immediately subsequent comparison, by the image storage section.

7. A pattern inspection apparatus comprising: an image capturing section for capturing images, by scanning an object to be inspected on which a plurality of patterns having a cell pattern to be repeated at a predetermined pitch are arranged, of the plurality of patterns; and m (m is an integer larger than 1) processing units having an identical configuration, wherein each processing unit comprises an image storage section for storing the captured images, a positional information detecting section for detecting the positional information of the images of the identical patterns in each row, a correction quantity determining section for determining the quantity of correction, by which a positional relation of the images of the neighboring identical patterns is corrected, based on the detected positional information, a pattern comparison section for correcting the positional relation based on the quantity of correction and comparing the corrected images, and a cell comparison section for making a comparison between the neighboring cell patterns in each pattern, and wherein each of the m processing units carries out, for each row and in a sharing manner, any of the capture and storage of the images, the cell comparison and the detection of positional deviation, and the determination of the quantity of correction and the pattern comparison, and take turns for each capture and storage of the images.

8. A pattern inspection apparatus, as set forth in claim 7, wherein the correction quantity determining section determines the quantity of correction based on the positional information of images of multiple separate patterns in each row in the scanning direction in the pattern arrangement.

9. A pattern inspection apparatus, as set forth in claim 8, wherein the multiple separate patterns include the patterns on both ends in each die.

* * * * *